(12) United States Patent
Handa et al.

(10) Patent No.: US 10,994,007 B2
(45) Date of Patent: May 4, 2021

(54) IMMUNITY INDUCER

(71) Applicants: Hiroshi Handa, Tokyo (JP); Saitama Medical University, Saitama (JP); SYSMEX CORPORATION, Kobe (JP)

(72) Inventors: Hiroshi Handa, Tokyo (JP); Masaaki Kawano, Saitama (JP); Masahiko Kato, Kobe (JP)

(73) Assignees: Saitama Medical University, Saitama (JP); SYSMEX CORPORATION, Kobe (JP)

(*) Notice: Subject to any disclaimer, the term of this patent is extended or adjusted under 35 U.S.C. 154(b) by 206 days.

(21) Appl. No.: 15/363,748

(22) Filed: Nov. 29, 2016

(65) Prior Publication Data

US 2017/0151326 A1   Jun. 1, 2017

(30) Foreign Application Priority Data

Nov. 30, 2015 (JP) .............................. JP2015-234206

(51) Int. Cl.
| | |
|---|---|
| *A61K 39/12* | (2006.01) |
| *A61K 39/39* | (2006.01) |
| *C12N 7/00* | (2006.01) |
| *C07K 14/005* | (2006.01) |
| *A61K 39/00* | (2006.01) |

(52) U.S. Cl.
CPC ............ *A61K 39/39* (2013.01); *C07K 14/005* (2013.01); *C12N 7/00* (2013.01); *A61K 2039/5256* (2013.01); *A61K 2039/5258* (2013.01); *A61K 2039/54* (2013.01); *A61K 2039/542* (2013.01); *A61K 2039/543* (2013.01); *A61K 2039/572* (2013.01); *A61K 2039/575* (2013.01); *C07K 2319/00* (2013.01); *C07K 2319/43* (2013.01);

(Continued)

(58) Field of Classification Search
None
See application file for complete search history.

(56) References Cited

U.S. PATENT DOCUMENTS

| | | |
|---|---|---|
| 2008/0131928 A1 | 6/2008 | Handa et al. |
| 2009/0298955 A1 | 12/2009 | Handa et al. |

(Continued)

FOREIGN PATENT DOCUMENTS

| | | |
|---|---|---|
| WO | 2006/004173 A1 | 1/2006 |
| WO | 2006/088229 A1 | 8/2006 |
| WO | 2012/157408 A1 | 11/2012 |

OTHER PUBLICATIONS

Shin et al., "Formation of Polyomavirus-Like Particles with Different VP1 Molecules that Bind the Urokinase Plasminogen Activator Receptor," Journal of Virology, vol. 77, No. 21: 11491-11498 (2003).*

(Continued)

*Primary Examiner* — M Franco G Salvoza
(74) *Attorney, Agent, or Firm* — Sughrue Mion, PLLC

(57) ABSTRACT

Disclosed is an immunity inducer. The immunity inducer comprises virus like particles; the virus like particles comprise a virus-derived outer coat protein and an antigen-bound protein comprising an exogenous antigen; the outer coat protein constitutes an outer coat of the virus like particles, and the antigen-bound protein is comprised in the outer coat; and the virus like particles induce an immune effect of a living body on the antigen.

8 Claims, 8 Drawing Sheets

Figure 1:
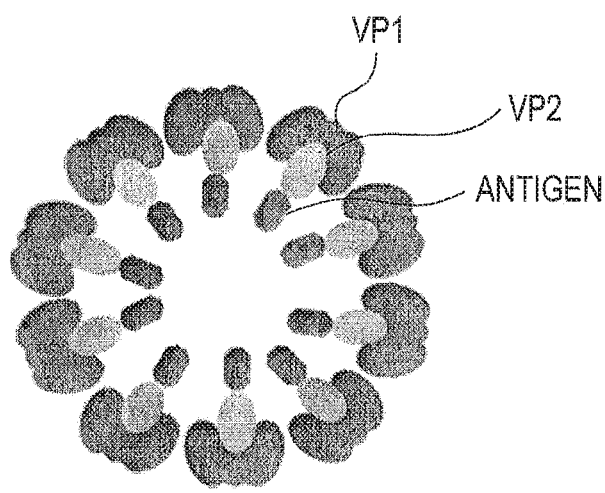

Specification includes a Sequence Listing.

(52) U.S. Cl.
CPC ............ *C12N 2710/22023* (2013.01); *C12N 2710/22034* (2013.01); *C12N 2760/16134* (2013.01)

(56) References Cited

U.S. PATENT DOCUMENTS

| | | | |
|---|---|---|---|
| 2012/0164710 A1* | 6/2012 | Fan | C07K 14/005 435/239 |
| 2013/0052216 A1* | 2/2013 | Steadman | A61K 39/145 424/192.1 |
| 2014/0286978 A1 | 9/2014 | Handa et al. | |

OTHER PUBLICATIONS

Roy et al., "Virus-like particles as a vaccine delivery system: Myths and facts," Human Vaccines, 4:1, 5-12 (2008).*
Lacksiene et al., "The Use of Recombinant Pseudotype Virus-Like Particles Harbouring Inserted Target Antigen to Generate Antibodies against Cellular Marker p16INK4A," The Scientific World Journal, Article ID 263737 (Year: 2012).*
Eriksson et al., "Murine Polyomavirus Virus-Like Particles Carrying Full-Length Human PSA Protect BALB/c Mice from Outgrowth of a PSA Expressing Tumor," PLoS ONE, vol. 6, Issue 8: e23828 (Year: 2011).*
Masaaki Kawano, et al., "Chimeric SV40 virus-like particles induce specific cytotoxicity and protective immunity against influenza A virus without the need of adjuvants", Virology, 2014, pp. 159-167, vol. 448.
Takamasa Inoue, et al. "Engineering of SV40-based nano-capsules for delivery of heterologous proteins as fusions with the minor capsid proteins VP2/3", Journal of Biotechnology, 2008, pp. 181-192, vol. 134.
Ryou-U Takahashi, et al. "Presentation of functional foreign peptides on the surface of SV40 virus-like particles", Journal of Biotechnology, 2008, pp. 385-392, vol. 135.
Communication, dated Mar. 27, 2017, issued by the European Patent Office in counterpart European Patent Application No. 16201293.4.
Tegerstedt, K. et al., "*A Single Vaccination with Polyomavirus VP1/VP2Her2 Virus-Like Particles Prevents Outgrowth of HER-2/neu-Expressing Tumors*", Cancer Research, vol. 65, No. 13, Jul. 1, 2005, pp. 5953-5957, (5 pages total).
Kawano M. et al, "*SV40 virus-like particles as an effective delivery system and its application to a vaccine carrier*", Expert Rev. Vaccines, vol. 12, No. 2, Feb. 9, 2013, pp. 199-210, (12 pages total).
Tegerstedt, K. et al. "*Murine Polyomavirus Virus-like Particles(VLPs) As Vectors for Gene and Immune Therapy and Vaccines against Viral Infections and Cancer*", Anticancer Research, vol. 25, No. 4, Jul. 1, 2005, pp. 2601-2608, (8 pages total).
Teunissen, E. et al., "*Production and biomedical applications of virus-like particles derived from polyoma viruses*", Journal of Controlled Release, vol. 172, No. 1, Aug. 31, 2013, pp. 305-321 (6 pages total).
Abbing A et al: "*Efficient Intracellular Delivery of a Protein and a Low Molecular Weight Substance via Recombinant Polyomavirus-like Particles*", The Journal of Biological Chemistry, vol. 279, No. 26, Jun. 25, 2004, pp. 27410-27421 (12 pages total).
Notice of Reasons for Refusal, dated Jun. 11, 2019, issued by the Japanese Patent Office in counterpart Japanese Patent Application No. 2015-234206.
Communication, dated Oct. 23, 2019, issued by the Japanese Patent Office in counterpart Japanese application No. 2015-234206.

* cited by examiner

*FIG. 2B* wt VP1-VLP/VP2-M1

100 nm

*FIG. 2C* wt VP1-VLP/VP2-M1

FMP: 58-66    (−)    (+)

INTRAPERITONEAL ADMINISTRATION    0.27    1.49

TRANSNASAL ADMINISTRATION    0.64    1.23

IFN-γ / CD8

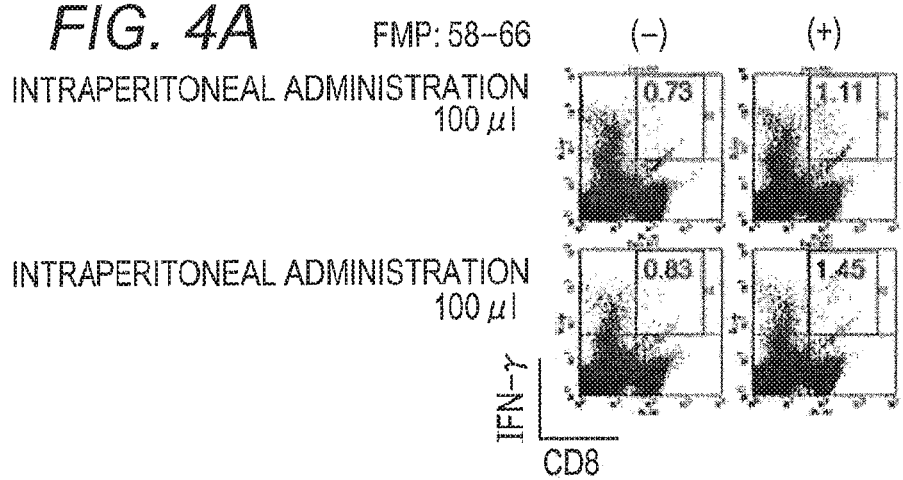
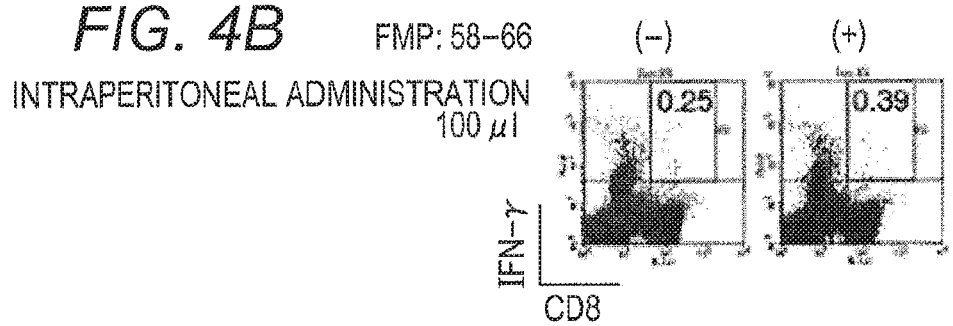
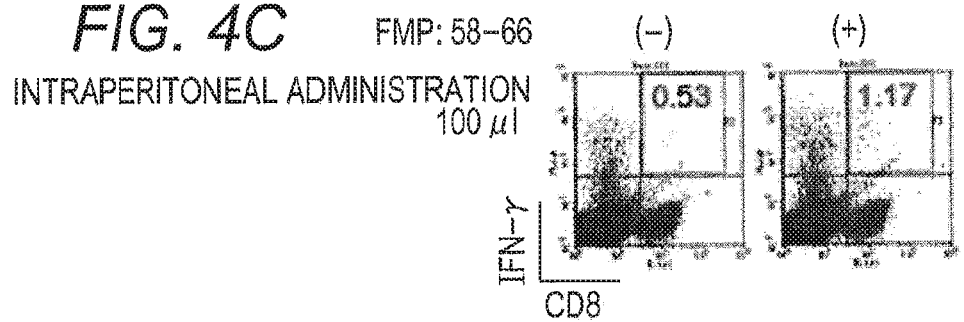
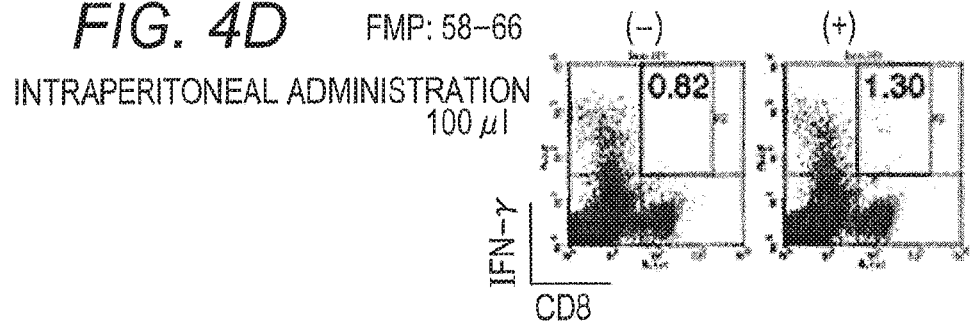

IMMUNITY INDUCER

CROSS REFERENCE TO RELATED APPLICATIONS

This application claims priority from prior Japanese Patent Application No. 2015-234206, filed on Nov. 30, 2015, entitled "IMMUNITY INDUCER AND METHOD FOR PRODUCING THE SAME", the entire contents of which are incorporated herein by reference.

TECHNICAL FIELD

The present invention relates to an immunity inducer. More specifically, the present invention relates to an immunity inducer comprising virus like particles.

BACKGROUND

It is known that a cytotoxic T lymphocyte (CTL) is induced using virus like particles, and viral diseases and cancer can be treated. For example, US Patent Application Publication No. 2014-0286978 describes that a CTL epitope-specific CTL can be induced by immunizing virus like particles obtained by introducing a CTL epitope into an SV40 VP1 loop region, and expressing it.

However, in US 2014-0286978, it is necessary to incorporate an epitope into a specific region of VP1, thus only an antigen in which epitope is publicly known can be used.

SUMMARY OF THE INVENTION

The scope of the present invention is defined solely by the appended claims, and is not affected to any degree by the statements within this summary.

As a result of intensive studies, the present inventors have found that an immune reaction of a living body can be induced even when using virus like particles including an antigen in its outer coat, thereby completing the present invention.

More specifically, the present invention provides an immunity inducer. The immunity inducer comprises virus like particles; the virus like particles comprise a virus-derived outer coat protein and an antigen-bound protein comprising an exogenous antigen; the outer coat protein constitutes an outer coat of the virus like particles, and the antigen-bound protein is comprised in the outer coat; and the virus like particles induce an immune effect of a living body on the antigen.

BRIEF DESCRIPTION OF THE DRAWINGS

FIG. 1 is a schematic view of an example of a virus like particle;

FIG. 2A is a SDS-PAGE photograph showing that VP2-M1 and wt VP1 are present in VLP purified from insect cells infected with a recombinant baculovirus;

FIG. 2B is an electron microscope photograph showing that VP2-M1/wt SV40 VP1 VLP is formed;

FIG. 2C is figures showing a result of ICS analysis performed for lymphocytes obtained from the spleen of a mouse administered with VP2-M1/wt SV40 VP1 VLP purified from insect cells;

FIG. 3 is a vector map of pM01 vector, depicting the multiple cloning site (MCS) sequence (SEQ ID NO: 16);

FIG. 4A is figures showing a result of ICS analysis performed for lymphocytes obtained from the spleen of a mouse intraperitoneally administered with a solution of ground silkworm pupa (phosphate buffer solution base) containing VP2-M1/wt SV40 VP1 VLP;

FIG. 4B is figures showing a result of ICS analysis performed for lymphocytes obtained from the spleen of a mouse intraperitoneally administered with a solution of ground silkworm pupa (Tris buffer solution base) containing VP2-M1/wt SV40 VP1 VLP;

FIG. 4C is figures showing a result of ICS analysis performed for lymphocytes obtained from the spleen of a mouse intraperitoneally administered with a solution of heat-treated ground silkworm pupa (phosphate buffer solution base) containing VP2-M1/wt SV40 VP1 VLP;

FIG. 4D is figures showing a result of ICS analysis performed for lymphocytes obtained from the spleen of a mouse intraperitoneally administered with a solution of heat-treated ground silkworm pupa (Tris buffer solution base) containing VP2-M1/wt SV40 VP1 VLP;

FIG. 5 is figures showing a result of ICS analysis performed for lymphocytes obtained from the spleen of a mouse nasally administered with a solution of ground silkworm pupa (phosphate buffer solution base) containing VP2-M1/wt SV40 VP1 VLP;

FIG. 6A is figures showing a result of ICS analysis performed for lymphocytes obtained from the spleen of a mouse orally administered with a solution of ground silkworm pupa (phosphate buffer solution base) containing VP2-M1/wt SV40 VP1 VLP;

FIG. 6B is figures showing a result of ICS analysis performed for lymphocytes obtained from the spleen of a mouse orally administered with a solution of ground silkworm pupa (Tris buffer solution base) containing VP2-M1/wt SV40 VP1 VLP;

FIG. 6C is figures showing a result of ICS analysis performed for lymphocytes obtained from the spleen of a mouse orally administered with a solution of heat-treated ground silkworm pupa (Tris buffer solution base) containing VP2-M1/wt SV40 VP1 VLP;

FIG. 7 is figures showing a result of ICS analysis performed for lymphocytes obtained from the spleen of a mouse intestinally administered with a solution of ground silkworm pupa (phosphate buffer solution base) containing VP2-M1/wt SV40 VP1 VLP;

FIG. 8A is a figure showing a measurement result of anti-OVA antibody production in the serum of a mouse intraperitoneally administered with VP2-OVA/wt SV40 VP1 VLP; and FIG. 8B is a figure showing a measurement result of anti-OVA antibody production in the serum of a mouse nasally administered with VP2-OVA/wt SV40 VP1 VLP.

DETAILED DESCRIPTION OF THE PREFERRED EMBODIMENTS

An immunity inducer of a present embodiment contains virus like particles containing a virus-derived outer coat protein and an antigen-bound protein.

A virus like particle is usually a structure that has no viral genome, as is well known in the art. The outer coat protein and inner peptide described below can use a protein derived from virus.

A schematic view of an example of a virus like particle contained in the immunity inducer of the present embodiment is shown in FIG. 1. The virus like particle represented by this schematic view has an outer coat constituted by outer coat protein VP1. An outer coat includes VP2 fused with an antigen. Both VP1 and VP2 are derived from SV40.

The kind of virus that is an origin of an outer coat protein and inner peptide is not particularly limited as long as it is a virus having at least one outer coat protein and at least one inner peptide. Examples of the kind of virus include viruses in the genus Polyomavirus (including SV40 (Simian virus 40), JC virus, BK virus and the like), viruses belonging to the Papillomavirus family (including α, β, γ and μ viruses in the genus Papillomaviruses and the like), viruses belonging to the Siphoviridae family of the order Caudovirales (including HK97 virus and the like), viruses belonging to the Reoviridae family (including rice dwarf virus (RDV), blue tongue virus and the like), viruses belonging to the Tombusviridae family (including tomato bushy stunt virus (TBSV) and the like), and the like. The virus is preferably a virus in the genus Polyomavirus, more preferably SV40, JC virus, BK virus or the like, and particularly preferably SV40. The outer coat protein and inner peptide are preferably derived from the same virus.

The genus Polyomavirus (Genus: Polyomavirus) means a genus in the virus classification published by International Committee on Taxonomy of Viruses (ICTV) in 2014.

In the virus classification, reorganization of the classification and modification of generic name or the like are often made. Accordingly, even when the classification is reorganized, or the generic name or the like is modified in the classification by ICTV or an equivalent academic authority in the future, viruses classified in the same genus as each virus belonging to the genus Polyomavirus in the ICTV classification in 2014 are defined to be included in the viruses in the genus Polyomavirus referred in this specification.

Since new kinds of viruses are often found in the art, new kinds of viruses that will belong to the current genus Polyomavirus or the classification group corresponding thereto are also defined to be included in the viruses in the genus Polyomavirus referred in this specification, in the virus classification by ICTV or an equivalent academic authority published in the future.

The orders, families, generic names and the like of the viruses referred above other than the genus Polyomavirus are also based on the ICTV classification published in 2014. The same as those stated for the genus Polyomavirus applies to the definition of these terms.

The outer coat protein is a protein that constitutes an outer coat of the virus like particles. The outer coat protein also can include an antigen-bound protein in the constituted outer coat. The phrase "the outer coat protein constitutes an outer coat of the virus like particles" means that the outer coat substantially comprises the outer coat protein. More specifically, the outer coat may be constituted only by an outer coat protein. Alternatively, the outer coat protein may be constituted by an outer coat protein and a peptide or protein bindable to the outer coat protein in a range in which the structure of outer coat is maintained. For example, the outer coat of wild-type SV40 virus is constituted by assembling of 72 VP1 pentamer units, and VP2 and VP3 are bound to the inside of the constituted outer coat as lining. However, VP1 of SV40 can constitute an outer coat by itself even without VP2 and VP3. In the present embodiment, the outer coat protein means a protein capable of substantially constituting an outer coat by themselves like SV40 VP1. The outer coat protein can be a peptide or protein containing at least an amino acid sequence minimally required to outer coat formation among virus-derived full-length amino acid sequences. The outer coat protein is preferably a protein having full-length amino acid sequences. Examples of such outer coat proteins include outer coat proteins of viruses belonging to the genus Polyomavirus, the Papillomavirus family, the Siphoviridae family of the order Caudovirales, the Reoviridae family and the Tombusviridae family, and more specific examples include VP1 of SV40 (Simian virus 40), JC viruses and the like that are viruses in the genus Polyomavirus, L1 of viruses belonging to the Papillomavirus family, P8 of rice dwarf virus (RDV), and the like. Examples of the peptide or protein at least containing an amino acid sequence minimally required to outer coat formation include 24mer peptides forming a tomato bushy stunt virus (TBSV)-derived (3-annulus structure, and the like. The outer coat protein is more preferably an outer coat protein of a virus in the genus Polyomavirus, further preferably an outer coat protein of SV40, JC virus, BK virus or the like, and particularly preferably SV40 VP1. The outer coat protein can be one or more kinds.

A protein that is a member constituting the outer coat in a wild-type virus like VP2 and VP3 of SV40, and cannot constitute the outer coat by themselves can be included in "inner peptide" described below, in the present embodiment. However, it does not mean that other substrates including "inner peptide" like VP2 and VP3 of SV40 are excluded from constituents of the outer coat. Such other substrates may be a non-essential member constituting the outer coat, or may involve in formation of the outer coat in some form.

The term "include" refers to the state that at least antigen in the antigen-bound protein is present in the inside of the outer coat formed by the outer coat protein.

The outer coat protein is not required to have completely same amino acid sequence as that of a wild-type virus. The amino acid sequence may be varied as long as it does not hinder outer coat formation and an antigen-bound protein can be included in the formed outer coat. Variation of amino acid sequence means that one or more amino acid residues are substituted, deleted or added as compared to the wild-type sequence. The outer coat protein may form an outer coat by its self-assembling ability. The outer coat protein may form an outer coat by the action of factors inherent in a host. The outer coat protein may form an outer coat, as monomers. The outer coat protein may form outer coat-forming units (capsomere) constituted from multimers and form an outer coat by assembling of the units. The outer coat protein forms an outer coat by assembling of preferably dimers to decamers and more preferably trimers to pentamers of about 50 to 500 capsomeres. The outer coat protein may be an extracted and purified natural protein. The outer coat protein may be artificially synthesized by a genetic engineering technique or the like.

The shape of outer coat is not particularly limited. The shape may be spherical or tubular. The shape of outer coat is, for example, approximately spherical, regular octahedron to regular icosahedron.

When the outer coat is constituted from monomers of outer coat protein, the number of monomers constituting one outer coat is not particularly limited. The number of monomers constituting one outer coat is preferably 100 to 1000 and more preferably 150 to 500.

When the outer coat is constituted from capsomeres, the number of capsomeres constituting one outer coat is preferably 50 to 390 and more preferably 72 to 260.

The diameter of outer coat is not particularly limited. The diameter of outer coat is preferably 30 to 300 nm and more preferably 45 to 200 nm.

The antigen-bound protein is a fusion protein of an antigen and a inner peptide. The antigen-bound protein contains an amino acid sequence of a desired antigen and an amino acid sequence of a virus-derived inner peptide. The inner peptide is not particularly limited as long as it constitutes the virus like particles of the present embodiment. The inner peptide contains at least an amino acid sequence necessary for constituting the virus like particles of the present embodiment, among virus-derived full-length amino acid sequences. The inner peptide preferably has full-length amino acid sequences. Examples of the inner peptide include VP2 and VP3 of SV40 (Simian virus 40), JC viruses and the like, L2 of viruses belonging to the Papillomavirus family, P3 of RDV, and the like. Examples of the peptide containing at least an amino acid sequence necessary for constituting the virus like particles of the present embodiment, among the virus-derived full-length amino acid sequences, include peptides comprising an amino acid sequence of SEQ ID No. 8 (specifically, peptides comprising a VP1 binding domain common to VP2 and VP3 of SV40), and the like. The inner peptide is more preferably a protein having an amino acid sequence of SEQ ID No. 9, and is further preferably a protein comprising an amino acid sequence of SEQ ID No. 9 or 11 (specifically, each of VP3 and VP2 of SV40; nucleic acid sequences are each shown in SEQ ID Nos. 10 and 12). The inner peptide can be one or more kinds.

The inner peptide may have completely the same amino acid sequence as that of a wild-type virus. The amino acid sequence may be varied as long as it constitutes the virus like particles of the present embodiment. The inner peptide may bind to the inside of the outer coat protein so as to form a lining of an outer coat. The inner peptide may be included in an outer coat without binding to the outer coat protein. The inner peptide may form an inner coat in the inside of the outer coat, for example, like P3 of RDV. In an embodiment using the inner peptide forming an inner coat, the term "inner" is used as long as it is present in the outer coat. A part of the inner peptide may be exposed from the outer coat. To the inner peptide may be added, for example, a tag for confirming expression of the antigen-bound protein, for example, a FLAG tag or the like.

In a preferred embodiment, the virus is the genus Polyomavirus SV40. In this embodiment, the outer coat protein is VP1, and the antigen-bound protein is a fusion protein of VP2 and/or VP3 and an antigen. VP1 is also called a major capsid protein, and VP2 and VP3 are also called a minor capsid protein. When using VP1 and VP2 and/or VP3 of SV40, VP2 and VP3 bind to the inside of the outer coat protein VP1 so as to form a lining of an outer coat. Generally, an outer coat of virus is often called capsid, thus a protein involved in outer coat formation like VP2 and VP3 of SV40 and the like can be also understood as an outer coat protein in a broad sense. However, in the present embodiment, a protein constituting an outer coat itself by itself, like VP1 of SV40, is called as "outer coat protein". Namely, even a protein that may be generally called as an outer coat protein or capsid protein is sometimes included in "inner peptide" in this specification, like VP2 and VP3 of SV40. In the present embodiment, an antigen can be included in an outer coat by binding the antigen to VP2 and/or VP3.

The kind of antigen is not particularly limited, and examples thereof include polypeptides, sugar chains, nucleic acids, lipids, and the like. The antigen is exogenous. The term "exogenous antigen" means the antigen is not derived from a virus from which the outer coat protein and inner peptide are derived and is not derived from a living body to which the immunity inducer is administered. The outer coat protein and the inner peptide are not included in "antigen" in this specification. Among them, polypeptides are preferred. When using a polypeptide as an antigen, a fusion protein containing an antigen and a inner peptide can be easily produced by a genetic engineering method.

As an antigen, it is preferred to use a polypeptide derived from a pathogen. The polypeptide derived from a pathogen may be a full-length polypeptide. The polypeptide derived from a pathogen may be a polypeptide containing only a part of sequences. Examples include HA, NA, M1, M2, NP, NS1, NS2, PA, PB1, PB2, PB1-F2 and the like of influenza viruses, Gag, Pol, Env, Tat, Nef, Rev and the like of HIV, E1, E2, Core, NS2, NS3, NS4, NS5 and the like of hepatitis C viruses (HCV), E6, E7 and the like of viruses belonging to the Papillomavirus family, Melan-A/MART-1, gp100, MAGEA3, MAGE-A10, CEA, HER2/new, NY-E50-1, WT-1, hTERT and the like that are proteins specific to cancer cells, and the like. Among them, M1, NP, NS1, PA, PB1 and PB2 of influenza viruses, HER2/new, WT-1 and MAGE-A3 that are proteins specific to cancer cells and the like are preferred.

The antigen binds to a inner peptide so as to be included in the outer coat of the virus like particles. Conventionally, virus like particles in which an antigen epitope is incorporated into a part in an outer coat protein exposed to the outside of the outer coat when the outer coat protein forms the outer coat (specifically, virus like particles in which an epitope is incorporated into a DE loop or an HI loop of SV40 VP1) are known (Patent Document 1). In this case, when the amino acid length of the antigen epitope to be incorporated is too long, the outer coat structure can be destroyed, and it is necessary to incorporate the epitope into a specific region of the outer coat protein. Thus, only an antigen with a short epitope (about 5 to 15 amino acids) in which its sequence is publicly known can be practically used. On the other hand, in present embodiment, an antigen is included in an outer coat, thus it becomes possible to include an antigen having longer amino acid length, as compared to a method of incorporating conventional epitope into the outer coat structure. Thus, a full-length antigen can be also used. Moreover, it is possible to induce immunity without adding an adjuvant to an antigen. The present inventors have unexpectedly found this point.

The size of the antigen is not particularly limited as long as it can be included in an outer coat. The size of the antigen is preferably 200 to 600 amino acid length.

The method of fusing an antigen and a inner peptide is not particularly limited, and a method known to a person skilled in the art, for example, a gene recombination technique and the like can be used. An antigen and a inner peptide may be fused via one or more linkers known to a person skilled in the art, for example, a GGGGS linker (residues 1-5 of SEQ ID NO: 3).

An immunity inducer of the present embodiment induces an immune effect of a living body on an antigen included in an outer coat of virus like particles. The phrase "induces an immune effect" refers to activation of immunity of a living body by inducing an antibody or a cytotoxic T lymphocyte. For example, an action of producing an antibody by administration to a living body prior to onset of a disease (cancer, etc.) or infection of a pathogen (virus, etc.) and/or an action of inducing a memory CTL is enhanced to prevent a future disease (use as a preventive vaccine), and a cytotoxic T lymphocyte (CTL) of a living body is induced by administration to a living body having a disease (cancer, infection, etc.) to treat the disease (use for immunotherapy), and the like.

An immunity inducer can be used as a vaccine for preventing or treating viral diseases or a vaccine for preventing or treating various cancers. Specifically, an immunity inducer can be used as a vaccine for preventing or treating diseases such as infections (influenza, immunodeficiency syndrome, hepatitis C, etc.), cancers (cervical cancer, pharyngeal papilloma, etc.), verrucas (verruca vulgaris, inclusion body of verruca vulgaris, verruca plana, etc.), HPV-associated epidermoid cyst, epidermodysplasia verruciformis, condyloma acuminatum and bowenoid papulosis.

In the immunity inducer, virus like particles may be formulated with a pharmaceutical additive known to a person skilled in the art. The pharmaceutical additive as described above is not particularly limited, and examples thereof include excipients, lubricants, binders, disintegrants, coating agents, capsule base materials, plasticizers, colorants, solvents, stabilizers, preservatives, buffers, analgesics, bases, emulsifiers and suspending agents, other corrigents, sweeteners, absorbents, dissolution adjuvants, pH adjusting agents, thickeners, tonicity agents, dispersants, antiseptics, wetting agents, flavoring agents, antioxidants, and the like.

The excipient is not particularly limited, and examples thereof include mannitol, sucrose, glucose, corn starch, crystalline cellulose, calcium hydrogen phosphate, and the like.

The lubricant is not particularly limited, and examples thereof include magnesium stearate, talc, colloidal silica, and the like.

The binder is not particularly limited, and examples thereof include gum arabic, hydroxypropylcellulose (HPC), hydroxypropylmethylcellulose (HPMC), methylcellulose (MC), povidone (PVP), polyvinyl alcohol (PVA), and the like.

The disintegrant is not particularly limited, and examples thereof include cross-linked carmellose sodium, carmellose calcium, cross-linked povidone, sodium carboxymethyl starch, and the like.

The coating agent is not particularly limited, and examples thereof include coating agents for sugar coating such as sucrose and talc, enteric coating agents such as carboxymethylethyl cellulose, gastrosoluble coating agents such as polyvinyl acetal diethyl aminoacetate, and the like.

The capsule base material is not particularly limited, and examples thereof include gelatin and the like.

The plasticizer is not particularly limited, and examples thereof include triacetin, medium-chain triglyceride, and the like.

The colorant is not particularly limited, and examples thereof include edible tar colors, lake pigments, iron sesquioxide, and the like.

The solvent is not particularly limited, and examples thereof include aqueous solvents such as water for injection and sterile purified water, nonaqueous solvents such as vegetable oils (including olive oil, soybean oil and sesame oil), and the like.

The stabilizer is not particularly limited, and examples thereof include inert gas such as nitrogen and carbon dioxide, chelating agents such as EDTA, reduction substrates such as L-ascorbic acid, and the like.

The preservative is not particularly limited, and examples thereof include p-oxybenzoic ester, chlorobutanol, and the like.

The buffer is not particularly limited, and examples thereof include sodium salts of citric acid, acetic acid, phosphoric acid, and the like.

The analgesic is not particularly limited, and examples thereof include benzyl alcohol, procaine hydrochloride, glucose, and the like.

The base is not particularly limited, and examples thereof include bases for suppositories such as cacao butter and gelatin, bases for ointments such as liquid paraffin and carnauba wax, and the like.

The emulsifier is not particularly limited, and examples thereof include gum arabic, polysorbate, sodium lauryl sulfate, and the like.

The suspending agent is not particularly limited, and examples thereof include gum arabic, sodium alginate, tragacanth, aluminum monostearate, and the like.

An immunity inducer has a sufficient immunity inducing effect by itself. Thus, an immunity inducer may not contain an adjuvant, but may contain an adjuvant. When an immunity inducer contains an adjuvant, examples of the adjuvant to be used include aluminum hydroxide gel, complete Freund's adjuvant, incomplete Freund's adjuvant, pertussis adjuvant, poly(I,C), CpG-DNA, and the like.

An immunity inducer may be any of a solid preparation, a semisolid preparation, a liquid preparation, an injection, a suppository, and other preparation form known to a person skilled in the art. Specific dosage form is not particularly limited, and examples thereof include tablets, pills, granules, powders, capsules, troches, injections, liquid agents, elixirs, syrups, limonades, suppositories, ointments, suspension agents, emulsions, liniments, lotions, percutaneous absorption preparations, patches, cataplasms, aerosols, and the like.

The liquid preparation is prepared, for example, by extracting virus like particles from a host cell expressing the virus like particles and diluting the virus like particles with an appropriate solvent as necessary.

The suspension agent is prepared, for example, by producing a homogenate obtained by homogenizing a host cell expressing the virus like particles, and extracting, purifying, and diluting the homogenate with a solvent as necessary. Specifically, when a lepidopterous insect individual such as a silkworm is used as a host, a suspension agent can be prepared by grinding an individual expressing the virus like particles, and roughly purifying the ground individual.

The administration route of an immunity inducer is not particularly limited, and examples thereof include oral administration, transmucosal administration (for example, transnasal administration, intranasal administration, buccal administration, enema administration, and the like), parenteral administration (for example, intraperitoneal injection, subcutaneous injection, intravenous injection, intramuscular injection, injection into a space between tissues, and the like), transdermal administration, and the like. More specifically, an immunity inducer of the present embodiment can be used by not only a high burden administration by injection or the like, but also a low burden administration by oral ingestion, administration by collunarium, enema or the like. For example, an immunity inducer can be used as a vaccine for animals by mixing into animal feed.

The dose and number of doses of an immunity inducer can be properly set by a person skilled in the art according to the kind of an antigen, animal species of an administration target, and symptom, age, body weight, administration form and the like, of an administration target. The dose is usually 0.01 µg to 100 mg, preferably 0.1 µg to 50 mg, and more preferably 1.0 µg to 10 mg, and it is preferred to administer an immunity inducer once per few days to few months.

The administration target of an immunity inducer can be biological bodies, more specifically, human or animals other than human (mammals other than human, birds, reptiles, and the like). Examples of animals other than human include bovine, equine, porcine, chicken, canine, feline, mouse, rat, lagomorph, simian, and the like.

An immunity inducer of the present embodiment is a pharmaceutical composition containing a pharmacologically effective amount of virus like particles from the viewpoint of immunity induction. Virus like particles may cause a pharmaceutically acceptable side effect when administered, but it is preferred for the animal of an administration target that there is no pathogenicity, and a side effect is not caused.

An immunity inducer of the present embodiment can be produced by preparing virus like particles according to a method known to a person skilled in the art, and formulating the virus like particles by mixing with a pharmaceutically acceptable excipient or the like as necessary.

Virus like particles can be prepared, for example, by mixing a virus-derived outer coat protein with an antigen-bound protein. Mixing conditions can be properly set by a person skilled in the art. An outer coat protein is mixed with an antigen-bound protein, whereby the antigen-bound protein is included in the outer coat formed by the outer coat protein.

Before preparing virus like particles, a DNA encoding an outer coat protein and a DNA encoding an antigen-bound protein are incorporated into a host cell, and the outer coat protein and the antigen-bound protein are expressed in the host cell, whereby the outer coat protein and the antigen-bound protein may be obtained. These proteins can be obtained by a method known to a person skilled in the art, for example, gene recombination and the like.

The host cell is not particularly limited as long as it does not hinder the formation of virus like particles. The host cell is selected, for example, from a group consisting of insect cells (including insect individuals such as silkworm), *Escherichia coli*, yeasts and plants. The host cell is preferably an insect cell, more preferably a lepidopterous insect individual, and further preferably a silkworm.

When an outer coat protein and an antigen-bound protein are expressed in a host cell, virus like particles may be prepared by contact of the outer coat protein with the antigen-bound protein expressed in the host cell. Alternatively, virus like particles may be formed in a production process such as homogenization, purification and extraction on the host cell.

The virus like particles formed in the host cell may be collected as necessary. Collection method is not particularly limited, but a person skilled in the art can properly selected mainly depending on the kind of the host cell. For example, when the host cell is an insect cell, an *Escherichia coli* cell or the like, cytolysis and the like by ultrasonication or the like can be used. When the host cell is a pupa of a lepidopterous insect, a method of eluting virus like particles by grinding or the like, and collecting a supernatant after centrifugation can be used.

In a preferred embodiment, first, an insect cell or insect individual is infected with a baculovirus into which a DNA encoding an outer coat protein and a DNA encoding an antigen-bound protein are incorporated. Next, the insect cell or insect individual is subjected to ultrasonic treatment or ground, then centrifuged or filtered, and the supernatant is collected, whereby virus like particles can be obtained. Alternatively, a host cell may be infected with a first baculovirus into which a DNA encoding an outer coat protein and a second baculovirus into which a DNA encoding an antigen-bound protein are incorporated, in place of the baculovirus into which a DNA encoding an outer coat protein and a DNA encoding an antigen-bound protein are incorporated.

The virus like particles may be purified as necessary. The purification method is not particularly limited, and examples thereof include methods known to a person skilled in the art such as density gradient centrifugation and chromatography and the like.

The virus like particles may be heat treated as necessary. The heat treatment method is not particularly limited, and examples thereof include methods of incubating silkworm pupae as a host cell in boiling water and the like.

Formulation can be performed, for example, by mixing virus like particles with an appropriate pharmaceutical additive, molding into a desired dosage form, and coating the dosage form as necessary.

Specifically, when a dosage form is formed into a solid preparation, for example, a tablet, it can be formulated, for example, by mixing virus like particles with an appropriate excipient, binder and/or disintegrant, adding an appropriate lubricant, further mixing the ingredients, tableting the mixture, and coating the dosage form as necessary.

When a dosage form is formed into an injection or a liquid preparation, it can be formulated, for example, by dispersing virus like particles in an appropriate solvent, filtering or sterilizing the dispersion as necessary, and filling the dispersion in a predetermined container.

When a dosage form is formed into an ointment, it can be formulated, for example, by melting an appropriate ointment in a mixer equipped with a warming device, stopping warming, mixing at a low speed until it coagulates in the form of an ointment, adding virus like particles immediately before coagulation, and filling the mixture in a predetermined container.

When a dosage form is formed into a suppository, it can be formulated, for example, by mixing virus like particles with an appropriate base for suppositories previously melted at a low temperature, pouring the mixture into a mold, and cooling it to harden.

Another embodiment relates to virus like particles for inducing an immune effect of a living body. More specifically, another embodiment relates to virus like particles containing a virus-derived outer coat protein and an antigen-bound protein, for inducing an immune effect of a living body on the antigen, in which the outer coat protein constitutes an outer coat of the virus like particles, and the antigen-bound protein is included in the outer coat.

The virus like particles, virus, outer coat protein, outer coat, antigen-bound protein, antigen and the like are as described above.

The virus like particles of the present embodiment can be used as a vaccine for preventing or treating viral diseases or a vaccine for preventing or treating various cancers, by being administered to a living body to induce an immune effect of the living body on an antigen included in the outer coat. Therefore, the virus like particles described above can be used as a vaccine for preventing or treating diseases such as infections (influenza, HIV, hepatitis C, etc.), cancers (cervical cancer, pharyngeal papilloma, etc.), verrucas (verruca vulgaris, inclusion body of verruca vulgaris, verruca plana, etc.), HPV-associated epidermoid cyst, epidermodysplasia verruciformis, condyloma acuminatum and bowenoid papulosis.

Accordingly, it can be also said that another embodiment relates to virus like particles for treating a disease. More specifically, the present embodiment relates to virus like particles containing a virus-derived outer coat protein and an antigen-bound protein, for treating a disease, in which the outer coat protein constitutes an outer coat of the virus like particles, and the antigen-bound protein is included in the outer coat.

The virus like particles, virus, outer coat protein, outer coat, antigen-bound protein, antigen, disease and the like are as described above.

Another embodiment relates to a method for inducing an immune effect of a living body including administering an immunity inducer containing virus like particles to the living body. More specifically, the present embodiment relates to a method for inducing an immune effect of a living body including administering an immunity inducer containing virus like particles to the living body, in which the virus like particles contain a virus-derived outer coat protein and an antigen-bound protein, the outer coat protein constitutes an outer coat of the virus like particles, and the antigen-bound protein is included in the outer coat, and induces an immune effect of the living body on the antigen.

The virus like particles, virus, outer coat protein, outer coat, antigen-bound protein, antigen, immunity inducer, administration method thereof, living body and the like are as described above.

It can be also said that another embodiment relates to a method for preventing or treating diseases including administering an immunity inducer containing virus like particles to a living body. More specifically, the present embodiment relates to a method for preventing or treating diseases including administering an immunity inducer containing virus like particles to a living body, in which the virus like particles contain a virus-derived outer coat protein and an antigen-bound protein, the outer coat protein constitutes an outer coat of the virus like particles, and the antigen-bound protein is included in the outer coat, and induces an immune effect of a living body on the antigen.

The virus like particles, virus, outer coat protein, outer coat, antigen-bound protein, antigen, immunity inducer, administration method thereof, living body, disease and the like are as described above.

Another embodiment relates to use of virus like particles in the production of an immunity inducer.

The virus like particles, virus, outer coat protein, outer coat, antigen-bound protein, antigen, immunity inducer, administration method thereof, living body, disease and the like are as described above.

Hereinbelow, the present invention will be described in detail by way of examples, but the present invention is not limited to these examples.

EXAMPLES

Example 1: Preparation of VP2-M1-Including SV40 VP1 VLP and Induction of FMP:58-66 Epitope Specific-Cytotoxic T Lymphocyte by Immunization Therewith Preparation of Baculovirus Expressing Wild-Type (Wt) Simian Virus 40 (SV40) VP1

A wt SV40 VP1 gene (SEQ ID No. 1; the amino acid sequence is shown in SEQ ID No. 2) was inserted into Sal I site and Kpn I site of pFastBac1 plasmid (INVITROGEN). *Escherichia coli* DH10bac (INVITROGEN) holding a baculovirus genome was transformed with the obtained plasmid to prepare a recombinant baculovirus genome with VP1 incorporated therein. The recombinant baculovirus genome was transfected to Sf-9 cells. After three days, the supernatant thereof was collected to obtain a solution containing recombinant baculovirus. A part of this solution was again infected with Sf-9 cells (invitrogen), thereby increasing a recombinant baculovirus titer. The resulting solution was referred to as a stock solution of recombinant baculovirus.

Preparation of Baculovirus Expressing VP2 Fused M1 Protein

A coding sequence of FLAG tag (SEQ ID No. 13) was added to the upstream of a codon encoding an amino terminus (N-terminus) of wt SV40 VP2, and a BamHI site was introduced into the further upstream thereof. The stop codon of wt SV40 VP2 was eliminated, and an EcoRI site was introduced. The obtained polynucleotide was inserted via a BamHI site and an EcoRI site of pFastBac1 plasmid to prepare a plasmid containing a wt SV40 VP2 gene. A coding sequence of a GGGGSGGGGSGGGGS linker (SEQ ID No. 3; the nucleic acid sequence is shown in SEQ ID No. 14) was introduced into the upstream of a codon encoding an N-terminus of M1 protein, and an EcoRI site was introduced into the further upstream thereof. The stop codon was added to the downstream of M1 protein coding sequence, and a Sal I site was introduced into the further downstream thereof. The obtained polynucleotide was introduced via the EcoRI site and the Sal I site of the plasmid containing a wt SV40 VP2 gene to prepare a plasmid holding a gene fused with the M1 coding sequence in the downstream of the VP2 coding sequence.

*Escherichia coli* DH10bac (INVITROGEN) holding a baculovirus genome was transformed with this plasmid to prepare a recombinant baculovirus genome expressing protein VP2-M1 in which M1 was fused with wt SV40 VP2 (SEQ ID No. 4; the nucleic acid sequence is shown in SEQ ID No. 5). These recombinant baculovirus genomes were transfected to Sf-9 cells. After three days, the supernatant thereof was collected to obtain a solution containing recombinant baculovirus.

A part of the solution obtained above was again infected with Sf-9 cells, thereby increasing a recombinant baculovirus titer. The resulting solution was referred to as a stock solution of recombinant baculovirus.

Preparation of Wt SV40 VP1 VLP Containing VP2-M1

A recombinant baculovirus with wt SV40 VP1 incorporated therein (M.O.I. (multiplicity of infection)=0.05 to 0.2) and a baculovirus with VP2-M1 incorporated therein (M.O.I.=0.015 to 0.06) were coinfected in a 15 cm culture dish in which 3×10$^7$ Sf-9 cells were inoculated (infection ratio of wt SV40 VP1:VP2-M1=1:0.3 (M.O.I. base)). A total of 10 dishes was prepared. After three days of infection, a total of 3×10$^8$ Sf-9 cells inoculated on these 10 dishes were collected. After washing with PBS (−), the cells were resuspended in 10 ml of a buffer for VP1 ultrasonic treatment (20 mM Tris-HCl (pH 7.9), 1% (w/vol) deoxycholic acid). Thereafter, in order to suppress endogenous protease activity, 2 mM phenylmethylsulfonyl fluoride (final concentration of 2 μM), chymostatin (final concentration of 1 μg/ml), aprotinin (final concentration of 1 μg/ml), leupeptin (final concentration of 1 μg/ml), antipain (final concentration of 1 μg/ml) and pepstatin (final concentration of 1 μg/ml) were added thereto, and the mixture was ultrasonically crushed.

Thereafter, the crushed substance was centrifuged at 15,000 rpm, 4° C. for 5 minutes to separate into supernatant and pellet, and the supernatant was referred to as a lysate solution.

Each 1.5 ml of a 20% CsCl solution (20 mM Tris-HCl (pH 7.9), 20% (w/vol) cesium chloride), a 30% CsCl solution (20 mM Tris-HCl (pH 7.9), 30% (w/vol) cesium chloride), a 40% CsCl solution (20 mM Tris-HCl (pH 7.9), 40% (w/vol) cesium chloride), and a 50% CsCl solution (20 mM Tris-HCl (pH 7.9), 50% (w/vol) cesium chloride) were superposed in an Ultra-Clear centrifugation tube (14×89 mm, BECKMAN COULTER) in descending order of density, for density gradient centrifugation of cesium chloride. Then, 5 ml of the lysate solution containing wt SV40 VP1 containing VP2-M1 was further superposed. Thereafter, the centrifugation tube was ultracentrifuged at 35,000 rpm, 4° C. for 3 hours (SW41Ti rotor, BECKMAN).

Figure 2A:
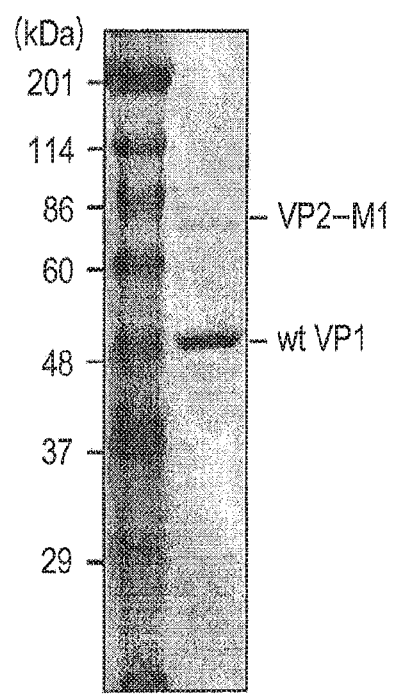
Figure 3:
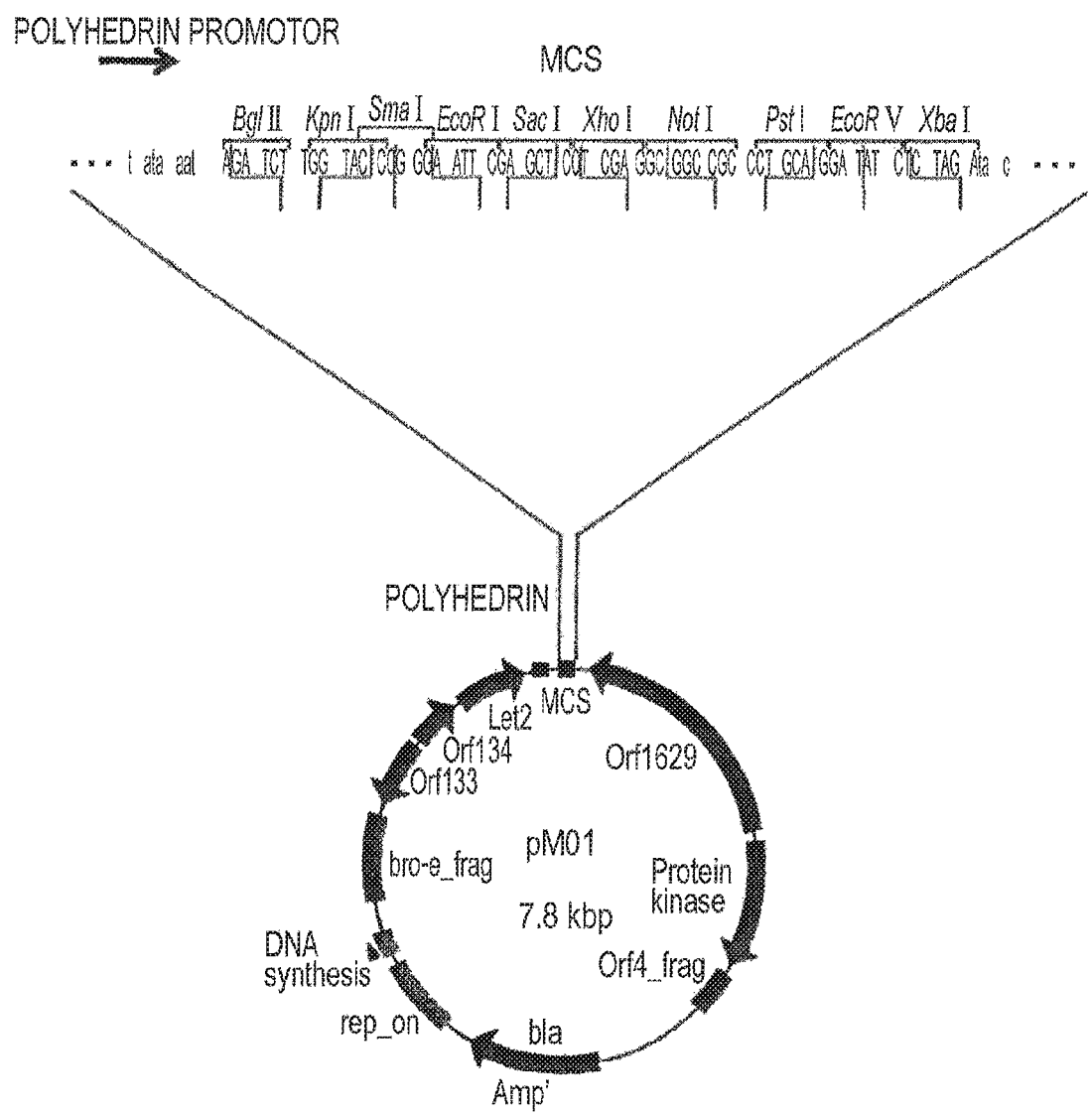
Figure 5:
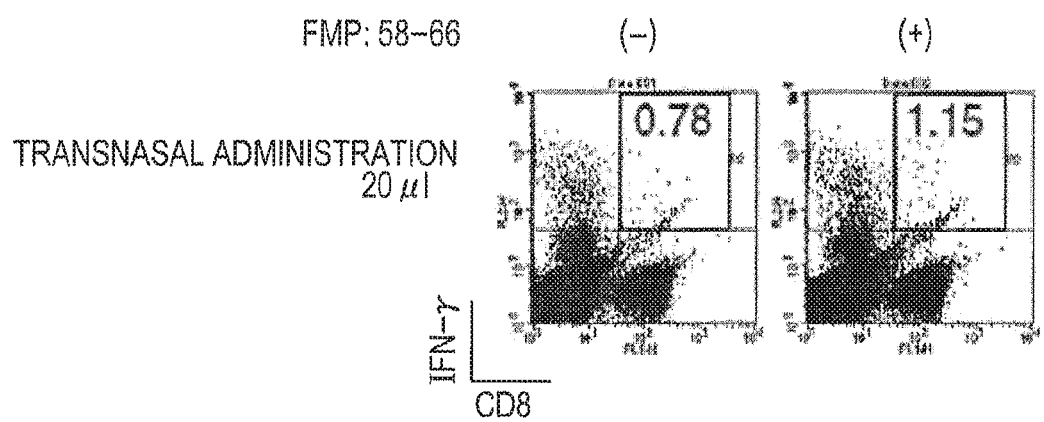

After ultracentrifugation, a white band appeared at a center was collected with 23 G, 1 ml of a Terumo syringe (0.60×32 mm, TERUMO). This fraction was mixed with a 37% CsCl solution (20 mM Tris-HCl (pH 7.9), 37% (w/vol) cesium chloride), and the mixture was transferred to an Ultra-Clear centrifugation tube (11×60 mm, Beckman coulter). Thereafter, the centrifugation tube was ultracentrifuged at 50,000 rpm, 4° C. for 20 hours (SW60Ti rotor, BECKMAN). After ultracentrifugation, a white band appeared at a center was collected with 23 G, 1 ml of a Terumo syringe (0.60×32 mm, TERUMO). This fraction was dialyzed (Slide-A-Lyzer MINI Dialysis Units, 3500 MWCO, THERMO SCIENTIFIC) against a PBS (−) solvent, and the fraction was centrifuged at 15,000 rpm, 4° C. for 5 minutes. The supernatant was collected and referred to as a wt SV40 VP1 VLP fraction containing purified VP2-M1. This fraction was developed by SDS-PAGE and then stained with CBB. As a result, it became certainly clear that two bands, a VP2-M1-derived band and a wt SV40 VP1 VLP-derived band, were purified (FIG. 2A). A VP2-M1- including wt SV40 VP1 VLP (VP2-M1/wt SV40 VP1 VLP) sample contained in this fraction was observed under an electron microscope photograph. As a result, VLP formed by wt SV40 VP1 could be confirmed (FIG. 2B). It was suggested that VP2-M1 was included in the inside of VLP.

Immunization of VP2-M1/wt SV40 VP1 VLP

The following experiment used a transgenic mouse using C57BL/6 as a background and expressing a chimera of HLA-A*0201 and H-2Db further fused with human β2m (hereinafter, HHD mouse). This mouse is a β2m and H-2Db knockout mouse, thus it is considered that mouse-derived MHC class I is not exposed to the cell surface.

An 8-week old transgenic mouse was immunized by 100 μl of the VP2-M1/wt SV40 VP1 VLP (500 μg/ml) via the intraperitoneal route. For immunization, a 1 ml syringe with a 27-gauge needle inserted (Myjector™, syringe with an injection needle, for insulin, TERUMO, SS-10M2713) was used.

Alternatively, 40 μl of the VP2-M1/wt SV40 VP1 VLP (500 μg/ml) was nasally administered to an 8-week old transgenic mouse under general anesthesia, by the transnasal route.

One week after administration, the spleen of the immunized mouse was collected. Lymphocytes were prepared by the following method, and Intra-cellular staining (ICS) analysis described below was performed.

Preparation of Lymphocytes from Spleen of Mouse

The spleen was removed from the immunized mouse. The spleen was put in a φ6 cm dish with 5 ml of RPMI-1640 medium. The spleen was well loosened using tweezers in the medium, and a solution containing lymphocytes eluted in the medium was transferred to a 15 ml tube. The φ6 cm dish was again washed with 5 ml of RPMI-1640 medium. The supernatant was added to the 15 ml tube so that the total amount is 10 ml. The supernatant was again transferred to a new 15 ml tube, leaving tissue sections deposited at the bottom of the 15 ml tube. Thereafter, the 15 ml tube was centrifuged at 1,200 rpm at room temperature for 5 minutes to obtain a pellet containing lymphocytes. The supernatant was removed, and the pellet was loosened. Thereafter, in order to remove erythrocytes, 250 μl of a NH$_4$Cl-tris solution was added thereto, and the mixture was stirred. Thereafter, 10 ml of RPMI-1640 medium was quickly added thereto, and the 15 ml tube was centrifuged at 1,2000 rpm at room temperature for 5 minutes to obtain a pellet containing lymphocytes. The supernatant was removed, and the pellet was loosened. Thereafter, 10 ml of RPMI-1640 medium was again added thereto. The medium containing lymphocytes was transferred to a new 15 ml tube with a pipette so as not to suck modified erythrocytes as much as possible. Thereafter, the 15 ml tube was again centrifuged at 1,200 rpm at room temperature for 5 minutes. The supernatant was removed, and then the pellet was loosened. The pellet was again suspended in 10 ml of RPMI-1640 medium, and centrifuged at 1,200 rpm at room temperature for 5 minutes. The supernatant was removed, and the pellet was finally suspended in 2 ml of 10% FCS mixing RPMI-1640 medium. In order to count lymphocytes, 10 μl of the above suspension was added to 490 μl of a 2% acetic acid solution. The number of cells was counted with a Burker-Turk hemocytometer. The resulting mixture was diluted with 10% FCS mixing RPMI-1640 medium so as to be 1×10$^7$ cells/ml.

Intra-Cellular Staining (ICS) Analysis

After immunizing the mouse, ICS analysis was performed, in order to investigate that a CTL induced by reacting to M1 CTL epitope sequence (GILGFVFTL) (SEQ ID NO: 15) is present in the lymphocytes collected from the spleen. BD GolgiPlug™ (trademark) (BD) diluted 25-fold with 10% FCS mixing RPMI-1640 medium was added to a 96-well round-bottom plate, at 5 μl per well. Thereto was further added 100 μl of a peptide of 20 μM of M1 CTL epitope (GILGFVFTL, Operon) (SEQ ID NO: 15) diluted with 10% FCS mixing RPMI-1640 medium. As a negative control, 100 μl of a 10% FCS mixing RPMI-1640 medium not containing a peptide was added. To this well was added 100 μl of the lymphocytes prepared above. Thereafter, the mixture was incubated at 37° C., 5% CO$_2$, for 5 hours.

After incubation, the mixture was spun down at 4° C., 1,400 rpm to remove the supernatant, and the cells were loosened with a Vortex mixer. Thereafter, FACS buffer (2% FCS, 0.1% sodium azide, 1×PBS (−)) was added at 200 μl per well. The mixture was again spun down at 4° C., 1,400 rpm to remove the supernatant, and the cells were loosened. Thereafter, 100 μl of Mouse BD Fc Block™ (trademark) (BD PHARMINGEN) diluted to 5 μg/ml with FACS buffer was added thereto, and the mixture was incubated at 4° C. for 10 minutes.

After incubation, the mixture was again spun down at 4° C., 1,400 rpm to remove the supernatant, and the cells were loosened.

Thereafter, FACS buffer was added at 200 μl per well, and the mixture was again spun down at 4° C., 1,400 rpm to remove the supernatant. Washing operation with FACS buffer was again carried out. FITC Rat Anti-Mouse CD8a Clone: 53-6.7 (BD PHARMINGEN) diluted to 10 μg/ml with FACS buffer was added to the loosened cells, at 50 μl per well, and the mixture was incubated in a dark place at 4° C. for 30 minutes.

After incubation, washing operation with 200 μl of FACS buffer was carried out twice. Thereafter, 100 μl of BD Cytofix/Cytoperm™ (trademark) (BD BIOSCIENCES) was added to the loosened cells, at 100 μl per well, and the mixture was incubated in a dark place at 4° C. for 20 minutes. After incubation, the washing operation as same as described above was carried out twice, using 200 μl of 1×BD Perm/Wash™ (trademark) (BD BIOSCIENCES) in place of the FACS buffer. Thereafter, 50 μl of PE anti-mouse IFN-γClone: XMG1.2 (BIOLEGEND) diluted to 10 μg/ml with 1×BD Perm/Wash™ (trademark) was added to the loosened cells, and the mixture was incubated in a dark place at 4° C. for 30 minutes.

After incubation, the washing operation as same as described above was carried out twice, using 200 µl of 1×BD Perm/Wash™ (trademark). Thereafter, FACS fixation buffer (1% formaldehyde, 1×FACS buffer) was added to the loosened cells, at 100 µl per well, and the mixture was incubated in a dark place at 4° C. overnight.

After incubation, 400 µl of FACS buffer was added to 5 ml of a polystyrene tube (BD Falcon, 5 ml polystyrene round-bottom tube 12×75 mm style). Thereto was added the sample fixed with 100 µl of FACS fixation buffer. Thereafter, dot plot analysis was performed with FACScan (BD). Cell Quest™ (BD) software was used for the analysis. The result of ICS two-dimensional analysis is shown in FIG. 2C.

As a result of ICS analysis, CD8+IFN-γ+T cells appeared in an FMP:58-66 peptide addition dependent manner in immunization by the intraperitoneal (i.p.) route and immunization by the transnasal route. Based on the above, it became certainly clear that FMP:58-66 epitope specific-cytotoxic T lymphocyte (CTL) contained in M1 protein was induced by VP2-M1/wt SV40 VP1 VLP immunization (FIG. 2C).

Based on these results, it was shown that VP2-M1/wt SV40 VP1 VLP purified from insect cells was intraperitoneally or nasally administered to a HHD mouse, and M1 CTL epitope specific CTL could be induced.

Example 2: Induction of FMP:58-66 Epitope Specific-Cytotoxic T Lymphocyte by Immunization (Intraperitoneal, Transnasal, Oral, Enema Administration) of Solution of Ground Silkworm Pupa in which VP2-M1 and SV40 Wild-Type VP1 are Co-Expressed Preparation of VP2-M1 and Wt SV40 VP1 Co-Expressing Solution of Ground Silkworm Pupa A wt SV40 VP1 gene fragment was incorporated into a multicloning site (restriction enzyme SmaI) of pM01 vector (SYSMEX CORPORATION; the vector map is shown in FIG. 3). The resulting plasmid construct was called wt SV40 VP1 pM01.

A VP2-M1 gene was incorporated into a multicloning site (restriction enzyme SmaI) of pM01 vector (SYSMEX CORPORATION). The resulting plasmid construct was called VP2-M1 pM01.

A recombinant baculovirus was prepared by modifying a method of Maeda, et al. (Invertebrate Cell system and Applications, Vol. 1, p. 16'7-181, CRC Press, Boca Raton (1989)). Specifically, DNA (20 ng) of CPd baculovirus (cysteine protease deficient virus strain, SYSMEX) linearly linked to the above plasmid construct wt SV40 VP1 pM01 or VP2-M1 pM01 (each 50 ng) was co-transfected to BmN cells (Maeda, 1989), using a lipofection reagent (X-tremeGENE 9 DNA Transfection Reagent™: ROCHE DIAGNOSTICS K.K.). The infection symptoms were confirmed, and then the culture supernatant was collected. Whereby, a recombinant baculovirus incorporating a wt SV40 VP1 gene or VP2-M1 was obtained.

The recombinant baculovirus was inoculated to a silkworm pupa (variety: Kinsyu-showa, silkworm seeds were purchased from Ueda-sanshu and artificially bred to pupas in SYSMEX CORPORATION). After six days from virus inoculation, the pupas were collected, and frozen at −80° C.

To the frozen five pupas or five pupas incubated in boiled water for 10 minutes from a frozen state was added 25 mL of a Tris buffer (20 mM Tris-HCl (pH 8.0), 150 mM NaCl, 1 mM EDTA, 1 mM EGTA, 10% (w/v) glycerol, 1 mM DTT, protease inhibitor cocktail (ROCHE DIAGNOSTICS K.K., Complete-EDTA-free)), or a phosphate buffer solution (137 mM NaCl, 2.7 mM KCl, 8.1 mM $Na_2HPO_4$, 1.47 mM $KH_2PO_4$ (pH 7.4)). The pupas were crushed using a homogenizer (ELMEX LIMITED, Model SH-IIM, paddle crushing) to obtain a suspension. This suspension was filtered with a mesh to remove the residue of the epidermis of the pupa and the like, and this filtrate was referred to as a solution of ground silkworm pupa.

(Intraperitoneal Administration)

Immunization of VP2-M1/wt SV40 VP1 VLP

A 8-week HHD mouse was immunized by 100 μl of the homogenate prepared from silkworm expressing VP2-M1/wt SV40 VP1 VLP (a solution of ground silkworm pupa prepared with a phosphate buffer solution (FIG. 4A), a solution of ground silkworm pupa prepared with a Tris buffer solution (FIG. 4B), a solution of heat-treated ground silkworm pupa prepared with a phosphate buffer solution (FIG. 4C), and a solution of heat-treated ground silkworm pupa prepared with a Tris buffer solution (FIG. 4D)). For immunization, a 1 ml syringe with a 27-gauge needle inserted (Myjector, syringe with an injection needle, for insulin, TERUMO, SS-10M2713) was used.

One week after administration, the spleen of the immunized mouse was collected. Lymphocytes were prepared by the method described in Example 1, and Intra-cellular staining (ICS) analysis was performed.

As a result of ICS analysis, in i.p. immunization, appearance of CD8+IFN-γ+T cells was confirmed in an FMP:58-66 peptide addition dependent manner (FIGS. 4A to 4D). Based on these results, it became clear that FMP:58-66 epitope specific-cytotoxic T lymphocyte (CTL) contained in M1 protein was induced by i.p. immunization of the homogenate prepared from silkworm pupa expressing VP2-M1/wt SV40 VP1 VLP. This CTL induction was detected irrespective of the presence or absence of heat treatment of pupa, and irrespective of the kind of the buffer solution (Tris buffer solution or phosphate buffer solution) used in the preparation.

(Transnasal Administration)

Immunization of VP2-M1/Wt SV40 VP1 VLP

20 μl of the homogenate prepared from silkworm expressing VP2-M1/wt SV40 VP1 VLP was nasally administered to an 8-week old HHD mouse under general anesthesia, by the transnasal route. After one week from administration, the spleen of the immunized mouse was collected. Lymphocytes were prepared by the method described in Example 1, and Intra-cellular staining (ICS) analysis was performed.

As a result of ICS analysis, in nasal immunization, CD8+IFN-γ+T cells was appeared in an FMP:58-66 peptide addition dependent manner (FIG. 5). Based on the above, it became certainly clear that FMP:58-66 epitope specific-cytotoxic T lymphocyte (CTL) contained in M1 protein was induced by nasal immunization of VP2-M1/wt SV40 VP1 VLP.

(Oral Administration)

Immunization of VP2-M1/wt SV40 VP1 VLP

The silkworm homogenate expressing VP2-M1/wt SV40 VP1 VLP (100 μl of a solution of non-heated ground silkworm pupa prepared with a phosphate buffer solution (FIG. 6A), 100 μl of a solution of non-heated ground silkworm pupa prepared with a Tris buffer solution (FIG. 6B), and 100 μl of a solution of heat-treated ground silkworm pupa prepared with a Tris buffer solution (FIG. 6C)) was administered to a 8-week HHD mouse under general anesthesia by the oral route. For administration, a 1 ml syringe with an oral sonde (oral sonde needle for mouse, φ0.9×L50 mm (A), NATSUME SEISAKUSHO CO., LTD., KN-348) inserted (TERUMO) was used. After one week from administration, the spleen of the immunized mouse was collected. Lymphocytes were prepared by the method described in Example 1, and Intra-cellular staining (ICS) analysis was performed.

Figure 6A:
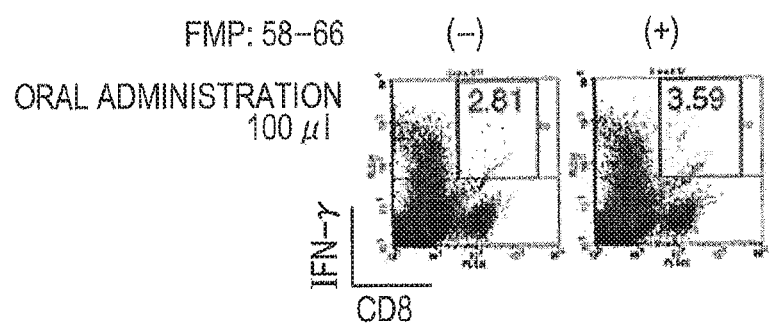
Figure 6B:
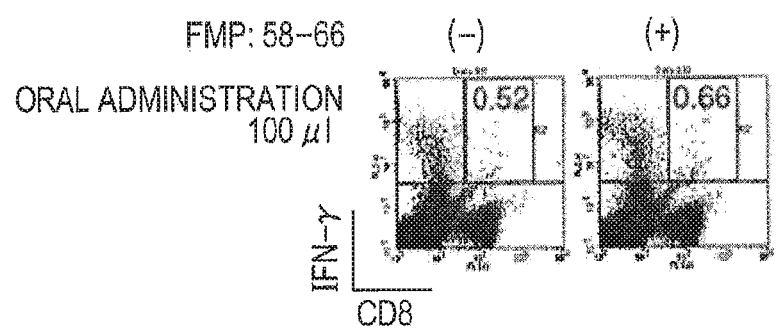
Figure 6C:
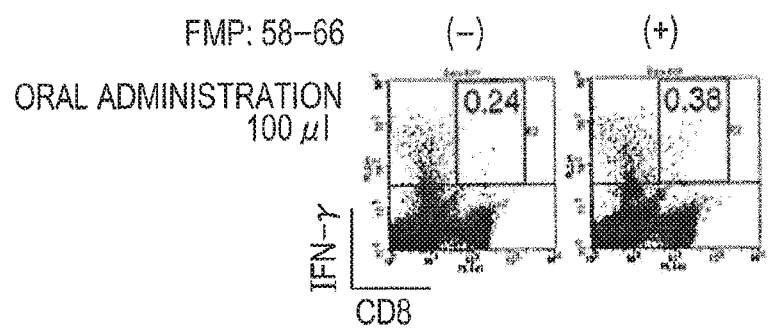

Based on the result of ICS analysis, CD8+IFN-γ+T cells were appeared in an FMP:58-66 peptide addition dependent manner in oral immunization (FIGS. 6A to 6C). Based on the above, it became certainly clear that FMP:58-66 epitope specific-cytotoxic T lymphocyte (CTL) contained in M1 protein was induced by oral immunization of the silkworm homogenate containing non-heated or heated VP2-M1/wt SV40 VP1 VLP.

(Enema Administration)
Immunization of VP2-M1/wt SV40 VP1 VLP

100 μl or 200 μl of the silkworm homogenate expressing VP2-M1/wt SV40 VP1 VLP was administered to an 8-week old HHD mouse under general anesthesia, by the enema route. For administration, a 1 ml syringe with an oral sonde (sterilized DISPOSABLE oral sonde for mouse, 5200S, FUCHIGAMI) inserted (TERUMO) was used.

After one week from administration, the spleen of the immunized mouse was collected. Lymphocytes were prepared by the method described in Example 1, and Intra-cellular staining (ICS) analysis was performed.

Figure 7:
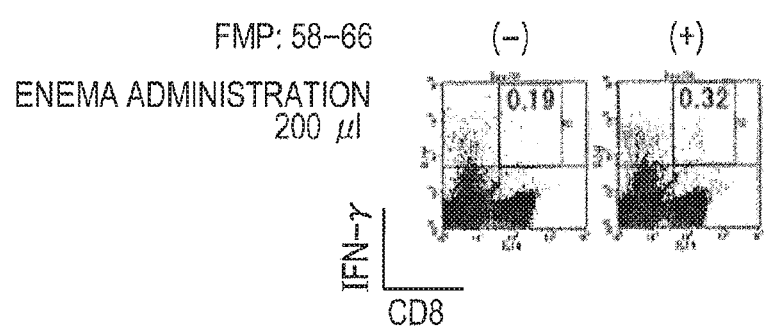

As a result of ICS analysis, CD8+IFN-γ+T cells were appeared in an FMP:58-66 peptide addition dependent manner in intestinal immunization (FIG. 7). Based on the above, it became certainly clear that FMP:58-66 epitope specific-cytotoxic T lymphocyte (CTL) contained in M1 protein was induced by VP2-M1/wt SV40 VP1 VLP immunization.

Example 3: Induction of Anti-OVA Antibody Production by Immunization with VP2-Egg Albumin (Ovalbumin, OVA)-Including Wt SV40 VP1 VLP Preparation of Baculovirus Expressing Wild-Type (Wt) Simian Virus 40 (SV40) VP1

A baculovirus expressing wt SV40 VP1 was prepared as described in Example 1.

Preparation of Baculovirus Expressing VP2 Fused OVA Protein

First, a coding sequence of FLAG tag (SEQ ID No. 13) was added to the upstream of a codon encoding an amino terminus (N-terminus) of wt SV40 VP2, and a BamHI site was introduced into the further upstream thereof. The stop codon of wt SV40 VP2 was eliminated, and an EcoRI site was introduced. The obtained polynucleotide was inserted via a BamHI site and an EcoRI site of pFastBac1 plasmid to prepare a plasmid containing a wt SV40 VP2 gene. A coding sequence of a GGGGSGGGGSGGGGS linker (SEQ ID No. 3; the nucleic acid sequence is shown in SEQ ID No. 14) was introduced into the upstream of a codon encoding an N-terminus of OVA protein, and an EcoRI site was introduced into the further upstream thereof. The stop codon was added to the downstream of OVA protein coding sequence, and a Sal I site was introduced into the further downstream thereof. The obtained polynucleotide was introduced via the EcoRI site and the Sal I site of the plasmid containing a wt SV40 VP2 gene to prepare a plasmid holding a gene fused with the OVA coding sequence in the downstream of the VP2 coding sequence.

*Escherichia coli* DH10bac (INVITROGEN) holding a baculovirus genome was transformed with this plasmid to prepare a recombinant baculovirus genome expressing protein VP2-OVA in which OVA was fused with wt SV40 VP2 (SEQ ID No. 6; the nucleic acid sequence is shown in SEQ ID No. 7). The recombinant baculovirus genome was transfected to Sf-9 cells. After three days, the supernatant thereof was collected to obtain a solution containing recombinant baculovirus. A part of this solution was again infected with Sf-9 cells, thereby increasing a recombinant baculovirus titer. The resulting solution was referred to as a stock solution of recombinant baculovirus.

Preparation of Wt SV40 VP1 VLP Containing VP2-OVA

A wt SV40 VP1 VLP containing VP2-OVA was prepared in the same manner as in "preparation of wt SV40 VP1 VLP containing VP2-M1" in Example 1.

Immunization of VP2-OVA/Wt SV40 VP1 VLP (Intraperitoneal Administration and Transnasal Administration)

An 8-week old HHD mouse was immunized by 100 μl of VP2-OVA/wt SV40 VP1 VLP (500 μg/ml) via the intraperitoneal route. For immunization, a 1 ml syringe with a 27-gauge needle inserted (Myjector™, syringe with an injection needle, for insulin, TERUMO, SS-10M2713) was used. 100 μL of an OVA solution (1 mg/mL) was subcutaneously inoculated to a mouse as an object group of VP2-OVA/wt SV40 VP1 VLP immunization.

Alternatively, 40 μl of VP2-OVA/wt SV40 VP1 VLP (500 μg/ml) was nasally administered to an 8-week old HHD mouse under general anesthesia, by the transnasal route.

After one week from immunization, additional immunization was performed. After two weeks from initial immunization, the mouse was given general anesthesia, then the blood was collected from the heart of the mouse. Blood clotting was induced in the obtained blood, and the mouse serum in the supernatant was collected.

Detection of Antibody Induced by Immunization (ELISA Method)

In order to confirm that an anti-OVA antibody induced in the serum by reaction to OVA is present, antibody detection was performed as follows, using the mouse serum collected as described above. OVA was dissolved in TBS (20 mM Tris-HCl (pH 8.0), 150 mM NaCl) so as to be 1 μg/100 μL. 100 μL of this solution was added to each well of a 96-well plate (NUNC MaxiSorp™ flat-bottom 96-well plate). The plate was allowed to stand at room temperature for 2 hours or at 4° C. overnight to bond OVA to the bottom surface of the plate. After OVA immobilization, the plate was washed with TBS-T (20 mM Tris-HCl (pH 8.0), 150 mM NaCl, 0.005% (w/v) Tween 20). Thereafter, 300 μL of a 5% (w/v) skim milk solution was added to each well, and the plate was allowed to stand at room temperature for 2 hours or at 4° C. overnight. The skim milk solution was removed, then each well was washed with TBS-T. 50 μL of a solution obtained by diluting the mouse serum obtained above to a desired concentration with TBS-T was added to each well, and the plate was allowed to stand at room temperature for 1 hour. The mouse serum solution was removed, and each well was washed with TBS-T. Thereafter, 100 μL of HRP-labeled anti-mouse IgG (H+L chain) (MEDICAL & BIOLOGICAL LABORATORIES CO., LTD.) diluted 2,000-fold with TBS-T, and the plate was allowed to stand at room temperature for 1 hour. After allowing the plate to stand, each well was washed with TBS-T. TMB peroxidase EIA complex substrate kit (BIO-RAD LABORATORIES, INC.) was added to each well according to the accompanying instructions, and HRP-labeled anti-mouse IgG (H+L chain) present in each well was measured. The absorbance value at 655 nm was measured using iMark™ microplate Absorbance Reader (BIO-RAD LABORATORIES, INC.).

Figure 8A:
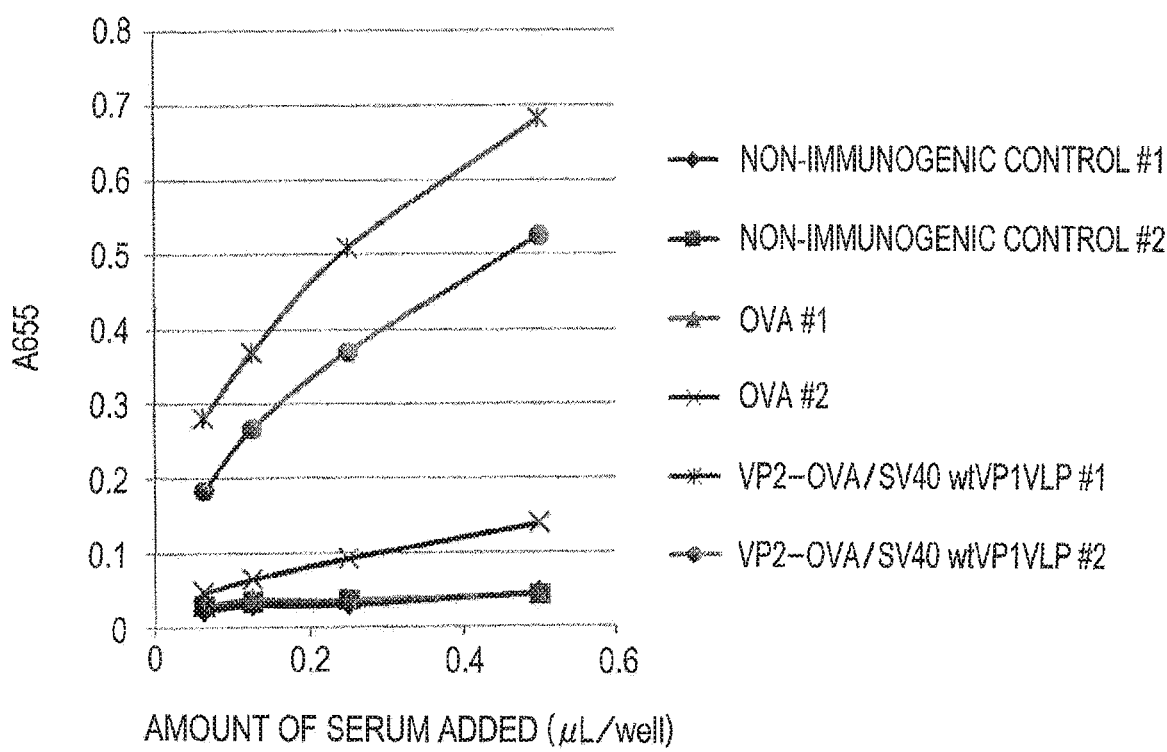
Figure 8B:
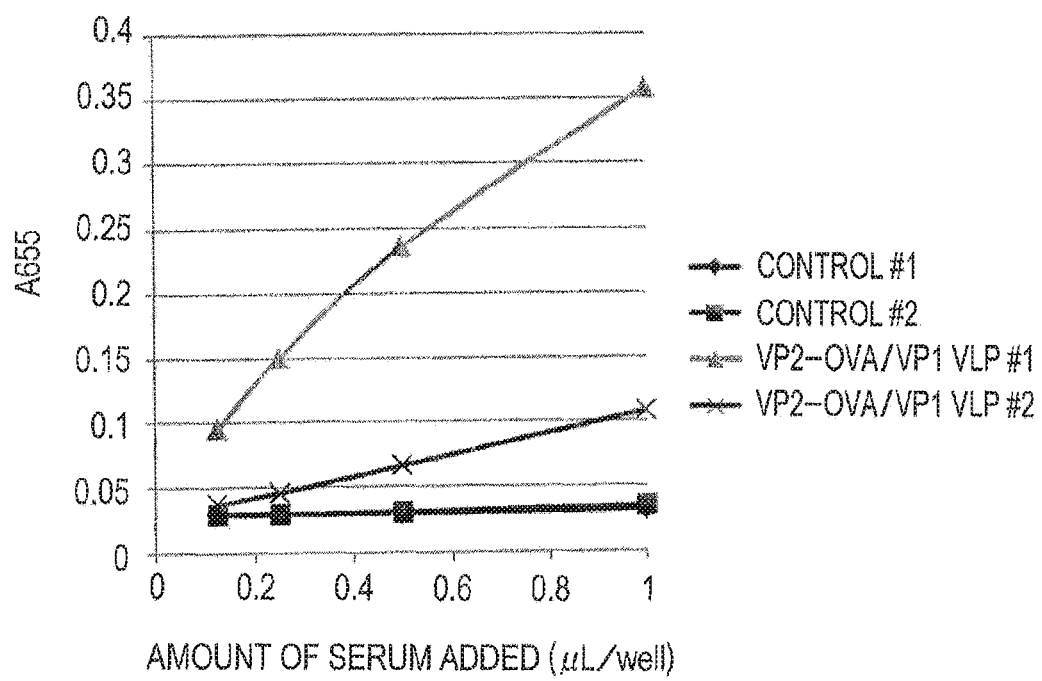

The results are shown in FIG. 8A and FIG. 8B. As shown in FIG. 8A, production of anti-OVA antibody was induced in a mouse intraperitoneally administered with VP2-OVA/SV40 wt VP1 VLP, and an antibody titer higher than a mouse singly administered with OVA was shown. Induction of anti-OVA antibody production was also seen in a mouse nasally administered with VP2-OVA/SV40 wt VP1 VLP (FIG. 8B). Based on these results, it was shown that production of an antibody specific to OVA can be induced by intraperitoneal administration or transnasal administration of VP2-M1/SV40 wt VP1 VLP.

What is claimed is:

1. A method of inducing immunity of a living body; comprising:
(1) administering a pharmacologically effective amount of an immunity inducer to the living body, and
(2) inducing in said living body, by said administration, an immune response against the exogenous antigen,
wherein the immunity inducer comprises virus like particles;
wherein the virus like particles comprise an outer coat protein constituting an outer coat of the virus like particles, and further comprise an antigen-bound protein comprising an exogenous antigen, wherein the virus like particles are virus like particles in which the amino acid sequence of the exogenous antigen is not inserted within the amino acid sequence of the outer coat protein, but the exogenous antigen is present inside the outer coat, and
wherein the administering step is conducted by oral administration, transmucosal administration, parenteral administration, or transdermal administration,
wherein the exogenous antigen is selected from the group consisting of: antigens from pathogens; and cancer antigens,
wherein the exogenous antigen is not exposed on the outer surface of said virus like particles,
wherein in the inducing step, a CTL and an antibody against the exogenous antigen are induced,
wherein the outer coat protein is VP1 of SV40, and
wherein the antigen-bound protein is a fusion protein of the exogenous antigen and an inner peptide, and the inner peptide is VP2 of SV40 and/or VP3 of SV40.

2. The method according to claim 1, wherein the amino acid sequence of the inner peptide comprises the amino acid sequence of SEQ ID NO: 9 or SEQ ID NO: 11.

3. The method according to claim 1, wherein the immunity inducer is a solid preparation, a semisolid preparation, a liquid preparation, an injection, or a suppository.

4. The method according to claim 1, wherein the amino acid sequence of the VP1 comprises the amino acid sequence of SEQ ID NO: 2.

5. The method according to claim 1, wherein
the amino acid sequence of the VP1 comprises the amino acid sequence of SEQ ID NO: 2,
the amino acid sequence of the VP2 comprises the amino acid sequence of SEQ ID NO: 11, and
the amino acid sequence of the VP3 comprises the amino acid sequence of SEQ ID NO: 9.

6. A method of inducing immunity of a living body; comprising:
(1) administering a pharmacologically effective amount of an immunity inducer to the living body, and
(2) inducing in said living body, by said administration, an immune response against the exogenous antigen,
wherein the immunity inducer comprises virus like particles;
wherein the virus like particles comprise an outer coat protein constituting an outer coat of the virus like particles, and further comprise an antigen-bound protein comprising an exogenous antigen, wherein the virus like particles are virus like particles in which the amino acid sequence of the exogenous antigen is not inserted within the amino acid sequence of the outer coat protein, but the exogenous antigen is present inside the outer coat, and
wherein the administering step is conducted by oral administration, transmucosal administration, parenteral administration, or transdermal administration,
wherein the exogenous antigen is selected from the group consisting of: antigens from pathogens; and cancer antigens,
wherein the exogenous antigen is not exposed on the outer surface of said virus like particles,
wherein in the inducing step, a CTL and an antibody against the exogenous antigen are induced,
wherein the outer coat protein is VP1 of SV40, and
wherein the antigen-bound protein is a fusion protein of the exogenous antigen and an inner peptide, and the inner peptide is VP2 of SV40.

7. The method according to claim 6, wherein the amino acid sequence of the VP1 comprises the amino acid sequence of SEQ ID NO: 2.

8. The method according to claim 6, wherein
the amino acid sequence of the VP1 comprises the amino acid sequence of SEQ ID NO: 2, and
the amino acid sequence of the VP2 comprises the amino acid sequence of SEQ ID NO: 11.

* * * * *

SEQUENCE LISTING

```
<160> NUMBER OF SEQ ID NOS: 16

<210> SEQ ID NO 1
<211> LENGTH: 1095
<212> TYPE: DNA
<213> ORGANISM: Polyomavirus SV40

<400> SEQUENCE: 1
atgaagatgg ccccaacaaa aagaaaagga agttgtccag gggcagctcc caaaaaacca      60
aaggaaccag tgcaagtgcc aaagctcgtc ataaaaggag aatagaagt tctaggagtt     120 aaaactggag tagacagctt cactgaggtg gagtgctttt taaatcctca atgggcaat     180 cctgatgaac atcaaaaagg cttaagtaaa agcttagcag ctgaaaaaca gtttacagat     240
gactctccag acaaagaaca actgccttgc tacagtgtgg ctagaattcc tttgcctaat     300
ttaaatgagg acttaacctg tggaaatatt ttgatgtggg aagctgttac tgttaaaact     360
gaggttattg gggtaactgc tatgttaaac ttgcattcag ggacacaaaa aactcatgaa     420
aatggtgctg gaaaacccat tcaagggtca aattttcatt tttttgctgt tggtggggaa     480
cctttggagc tgcagggtgt gttagcaaac tacaggacca aatatcctgc tcaaactgta     540
accccaaaaa atgctacagt tgacagtcag cagatgaaca ctgaccacaa ggctgttttg     600
gataaggata atgcttatcc agtggagtgc tgggttcctg atccaagtaa aaatgaaaac     660
actagatatt ttggaaccta cacaggtggg gaaaatgtgc ctcctgtttt gcacattact     720
aacacagcaa ccacagtgct tcttgatgag cagggtgttg ggcccttgtg caaagctgac     780
agcttgtatg tttctgctgt tgacatttgt gggctgttta ccaacacttc tggaacacag     840
cagtggaagg gacttcccag atattttaaa attacccta gaaagcggtc tgtgaaaaac     900
ccctacccaa tttcctttt gttaagtgac ctaattaaca ggaggacaca gagggtggat     960
gggcagccta tgattggaat gtcctctcaa gtagaggagg ttagggttta tgaggacaca    1020
gaggagcttc ctggggatcc agacatgata agatacattg atgagtttgg acaaaccaca    1080
actagaatgc agtga                                                      1095

<210> SEQ ID NO 2
<211> LENGTH: 364
<212> TYPE: PRT
<213> ORGANISM: Polyomavirus SV40

<400> SEQUENCE: 2

Met Lys Met Ala Pro Thr Lys Arg Lys Gly Ser Cys Pro Gly Ala Ala
1               5                   10                  15

Pro Lys Lys Pro Lys Glu Pro Val Gln Val Pro Lys Leu Val Ile Lys
                20                  25                  30

Gly Gly Ile Glu Val Leu Gly Val Lys Thr Gly Val Asp Ser Phe Thr
            35                  40                  45

Glu Val Glu Cys Phe Leu Asn Pro Gln Met Gly Asn Pro Asp Glu His
        50                  55                  60
```

```
Gln Lys Gly Leu Ser Lys Ser Leu Ala Ala Glu Lys Gln Phe Thr Asp
 65                  70                  75                  80

Asp Ser Pro Asp Lys Glu Gln Leu Pro Cys Tyr Ser Val Ala Arg Ile
                 85                  90                  95

Pro Leu Pro Asn Leu Asn Glu Asp Leu Thr Cys Gly Asn Ile Leu Met
            100                 105                 110

Trp Glu Ala Val Thr Val Lys Thr Glu Val Ile Gly Val Thr Ala Met
            115                 120                 125

Leu Asn Leu His Ser Gly Thr Gln Lys Thr His Glu Asn Gly Ala Gly
        130                 135                 140

Lys Pro Ile Gln Gly Ser Asn Phe His Phe Phe Ala Val Gly Gly Glu
145                 150                 155                 160

Pro Leu Glu Leu Gln Gly Val Leu Ala Asn Tyr Arg Thr Lys Tyr Pro
                165                 170                 175

Ala Gln Thr Val Thr Pro Lys Asn Ala Thr Val Asp Ser Gln Gln Met
            180                 185                 190

Asn Thr Asp His Lys Ala Val Leu Asp Lys Asp Asn Ala Tyr Pro Val
        195                 200                 205

Glu Cys Trp Val Pro Asp Pro Ser Lys Asn Glu Asn Thr Arg Tyr Phe
210                 215                 220

Gly Thr Tyr Thr Gly Gly Glu Asn Val Pro Pro Val Leu His Ile Thr
225                 230                 235                 240

Asn Thr Ala Thr Thr Val Leu Leu Asp Glu Gln Gly Val Gly Pro Leu
                245                 250                 255

Cys Lys Ala Asp Ser Leu Tyr Val Ser Ala Val Asp Ile Cys Gly Leu
            260                 265                 270

Phe Thr Asn Thr Ser Gly Thr Gln Gln Trp Lys Gly Leu Pro Arg Tyr
        275                 280                 285

Phe Lys Ile Thr Leu Arg Lys Arg Ser Val Lys Asn Pro Tyr Pro Ile
290                 295                 300

Ser Phe Leu Leu Ser Asp Leu Ile Asn Arg Arg Thr Gln Arg Val Asp
305                 310                 315                 320

Gly Gln Pro Met Ile Gly Met Ser Ser Gln Val Glu Glu Val Arg Val
                325                 330                 335

Tyr Glu Asp Thr Glu Glu Leu Pro Gly Asp Pro Asp Met Ile Arg Tyr
            340                 345                 350

Ile Asp Glu Phe Gly Gln Thr Thr Thr Arg Met Gln
        355                 360

<210> SEQ ID NO 3
<211> LENGTH: 15
<212> TYPE: PRT
<213> ORGANISM: Artificial Sequence
<220> FEATURE:
<223> OTHER INFORMATION: Synthetic GS linker peptide sequence

<400> SEQUENCE: 3

Gly Gly Gly Gly Ser Gly Gly Gly Ser Gly Gly Gly Gly Ser
1               5                   10                  15

<210> SEQ ID NO 4
<211> LENGTH: 638
<212> TYPE: PRT
<213> ORGANISM: Artificial Sequence
<220> FEATURE:
<223> OTHER INFORMATION: Synthetic peptide - VP2 protein fused with M1
      via a GS linker
```

```
<400> SEQUENCE: 4

Met Gly Ser Ser Asp Tyr Lys Asp Asp Asp Lys Ser Ser Gly Thr
1               5                   10                  15

Arg Met Gly Ala Ala Leu Thr Leu Leu Gly Asp Leu Ile Ala Thr Val
            20                  25                  30

Ser Glu Ala Ala Ala Ala Thr Gly Phe Ser Val Ala Glu Ile Ala Ala
            35                  40                  45

Gly Glu Ala Ala Ala Ala Ile Glu Val Gln Leu Ala Ser Val Ala Thr
        50                  55                  60

Val Glu Gly Leu Thr Thr Ser Glu Ala Ile Ala Ala Ile Gly Leu Thr
65                  70                  75                  80

Pro Gln Ala Tyr Ala Val Ile Ser Gly Ala Pro Ala Ala Ile Ala Gly
                85                  90                  95

Phe Ala Ala Leu Leu Gln Thr Val Thr Gly Val Ser Ala Val Ala Gln
                100                 105                 110

Val Gly Tyr Arg Phe Phe Ser Asp Trp Asp His Lys Val Ser Thr Val
            115                 120                 125

Gly Leu Tyr Gln Gln Pro Gly Met Ala Val Asp Leu Tyr Arg Pro Asp
    130                 135                 140

Asp Tyr Tyr Asp Ile Leu Phe Pro Gly Val Gln Thr Phe Val His Ser
145                 150                 155                 160

Val Gln Tyr Leu Asp Pro Arg His Trp Gly Pro Thr Leu Phe Asn Ala
                165                 170                 175

Ile Ser Gln Ala Phe Trp Arg Val Ile Gln Asn Asp Ile Pro Arg Leu
            180                 185                 190

Thr Ser Gln Glu Leu Glu Arg Arg Thr Gln Arg Tyr Leu Arg Asp Ser
        195                 200                 205

Leu Ala Arg Phe Leu Glu Glu Thr Thr Trp Thr Val Ile Asn Ala Pro
    210                 215                 220

Val Asn Trp Tyr Asn Ser Leu Gln Asp Tyr Tyr Ser Thr Leu Ser Pro
225                 230                 235                 240

Ile Arg Pro Thr Met Val Arg Gln Val Ala Asn Arg Glu Gly Leu Gln
                245                 250                 255

Ile Ser Phe Gly His Thr Tyr Asp Asn Ile Asp Glu Ala Asp Ser Ile
            260                 265                 270

Gln Gln Val Thr Glu Arg Trp Glu Ala Gln Ser Gln Ser Pro Asn Val
        275                 280                 285

Gln Ser Gly Glu Phe Ile Glu Lys Phe Glu Ala Pro Gly Gly Ala Asn
    290                 295                 300

Gln Arg Thr Ala Pro Gln Trp Met Leu Pro Leu Leu Gly Leu Tyr
305                 310                 315                 320

Gly Ser Val Thr Ser Ala Leu Lys Ala Tyr Glu Asp Gly Pro Asn Lys
                325                 330                 335

Lys Lys Arg Lys Leu Ser Arg Gly Ser Ser Gln Lys Thr Lys Gly Thr
            340                 345                 350

Ser Ala Ser Ala Lys Ala Arg His Lys Arg Arg Asn Arg Ser Ser Arg
        355                 360                 365

Ser Glu Phe Gly Gly Gly Ser Gly Gly Gly Ser Gly Gly Gly
    370                 375                 380

Gly Ser Met Ser Leu Leu Thr Glu Val Glu Thr Tyr Val Leu Ser Ile
385                 390                 395                 400

Ile Pro Ser Gly Pro Leu Lys Ala Glu Ile Ala Gln Arg Leu Glu Asp
                405                 410                 415
```

```
Val Phe Ala Gly Lys Asn Thr Asp Leu Glu Val Leu Met Glu Trp Leu
            420                 425                 430

Lys Thr Arg Pro Ile Leu Ser Pro Leu Thr Lys Gly Ile Leu Gly Phe
        435                 440                 445

Val Phe Thr Leu Thr Val Pro Ser Glu Arg Gly Leu Gln Arg Arg Arg
    450                 455                 460

Phe Val Gln Asn Ala Leu Asn Gly Asn Gly Asp Pro Asn Asn Met Asp
465                 470                 475                 480

Lys Ala Val Lys Leu Tyr Arg Lys Leu Lys Arg Glu Ile Thr Phe His
                485                 490                 495

Gly Ala Lys Glu Ile Ser Leu Ser Tyr Ser Ala Gly Ala Leu Ala Ser
            500                 505                 510

Cys Met Gly Leu Ile Tyr Asn Arg Met Gly Ala Val Thr Thr Glu Val
        515                 520                 525

Ala Phe Gly Leu Val Cys Ala Thr Cys Glu Gln Ile Ala Asp Ser Gln
    530                 535                 540

His Arg Ser His Arg Gln Met Val Thr Thr Thr Asn Pro Leu Ile Arg
545                 550                 555                 560

His Glu Asn Arg Met Val Leu Ala Ser Thr Thr Ala Lys Ala Met Glu
                565                 570                 575

Gln Met Ala Gly Ser Ser Glu Gln Ala Ala Glu Ala Met Glu Val Ala
            580                 585                 590

Ser Gln Ala Arg Gln Met Val Gln Ala Met Arg Thr Ile Gly Thr His
        595                 600                 605

Pro Ser Ser Ser Ala Gly Leu Lys Asn Asp Leu Leu Glu Asn Leu Gln
    610                 615                 620

Ala Tyr Gln Lys Arg Met Gly Val Gln Met Gln Arg Phe Lys
625                 630                 635
```

<210> SEQ ID NO 5
<211> LENGTH: 1917
<212> TYPE: DNA
<213> ORGANISM: Artificial Sequence
<220> FEATURE:
<223> OTHER INFORMATION: Synthetic polynucleotide - gene encoding VP2
fused with M1 via a GS linker

<400> SEQUENCE: 5

```
atgggcagca gcgactacaa ggacgacgat gacaagagca gcggcacgcg tatgggtgct     60
gctttaacac tgttggggga cctaattgct actgtgtctg aagctgctgc tgctactgga    120
ttttcagtag ctgaaattgc tgctggagag gccgctgctg caattgaagt gcaacttgca    180
tctgttgcta ctgttgaagg cctaacaacc tctgaggcaa ttgctgctat aggcctcact    240
ccacaggcct atgctgtgat atctggggct cctgctgcta tagctggatt tgcagcttta    300
ctgcaaactg tgactggtgt gagcgctgtt gctcaagtgg ggtatagatt ttttagtgac    360
tgggatcaca aagtttctac tgttggttta tatcaacaac caggaatggc tgtagatttg    420
tataggccag atgattacta tgatatttta tttcctggag tacaaacctt tgttcacagt    480
gttcagtatc ttgaccccag acattggggt ccaacacttt ttaatgccat ttctcaagct    540
ttttggcgtg taatacaaaa tgacattcct aggctcacct cacaggagct tgaaagaaga    600
acccaaagat atttaaggga cagtttggca aggtttttag aggaaactac ttggacagta    660
attaatgctc ctgttaattg gtataactct ttacaagatt actactctac tttgtctccc    720
attaggccta caatggtgag acaagtagcc aacagggaag ggttgcaaat atcatttggg    780
```

```
cacacctatg ataatattga tgaagcagac agtattcagc aagtaactga gaggtgggaa    840
gctcaaagcc aaagtcctaa tgtgcagtca ggtgaattta ttgaaaaatt tgaggctcct    900
ggtggtgcaa atcaaagaac tgctcctcag tggatgttgc ctttacttct aggcctgtac    960
ggaagtgtta cttctgctct aaaagcttat gaagatggcc ccaacaaaaa gaaaaggaag   1020
ttgtccaggg gcagctccca aaaaaccaaa ggaaccagtg caagtgccaa agctcgtcat   1080
aaaaggagga atagaagttc taggagtgaa ttcggtggtg gtggaagtgg tggtggtgga   1140
agtggtggtg gtggaagtat gtcactccta accgaagtcg agacttatgt cctgagcatt   1200
ataccgtcag gtcctctaaa agccgaaatt gcccagcgtt tagaggatgt gttcgcaggg   1260
aagaacactg accttgaggt gctgatggag tggctgaaaa cccgacccat tcttagccca   1320
cttaccaaag gcatcctggg attcgtgttc acactgactg ttccatctga gagaggcttg   1380
cagaggagac gatttgttca gaatgccctc aatgggaatg tgatcccaa caacatggac   1440 aaagccgtga agctttatcg caagctcaaa cgggagataa ccttccatgg agcgaaggaa   1500
atctccctca gttactctgc aggtgccttg gcgagctgta tgggcctgat ctacaatcgg   1560
atgggagccg tgacaacgga agtggctttt ggcctggtat gcgctacttg cgaacagatc   1620
gcagatagcc aacacaggtc ccacaggcag atggtcacca caaccaaccc tctgattcgg   1680
cacgagaaca atggtgtt agcgtccaca acggcaaaag ccatggaaca gatggccggc   1740
tcaagcgaac aagccgctga ggcaatggag gtagctagtc aggcaagaca gatggttcag   1800
gctatgagga ctatcgggac acatccctct tccagtgctg ggctgaagaa cgacctgttg   1860
gagaatctcc aagcctacca aaagcgcatg ggagtccaga tgcagcgctt taagtga     1917
```

<210> SEQ ID NO 6
<211> LENGTH: 772
<212> TYPE: PRT
<213> ORGANISM: Artificial Sequence
<220> FEATURE:
<223> OTHER INFORMATION: Synthetic peptide - VP2 fused with OVA via a GS linker

<400> SEQUENCE: 6

```
Met Gly Ser Ser Asp Tyr Lys Asp Asp Asp Lys Ser Ser Gly Thr
1               5                   10                  15

Arg Met Gly Ala Ala Leu Thr Leu Leu Gly Asp Leu Ile Ala Thr Val
            20                  25                  30

Ser Glu Ala Ala Ala Ala Thr Gly Phe Ser Val Ala Glu Ile Ala Ala
        35                  40                  45

Gly Glu Ala Ala Ala Ala Ile Glu Val Gln Leu Ala Ser Val Ala Thr
    50                  55                  60

Val Glu Gly Leu Thr Thr Ser Glu Ala Ile Ala Ile Gly Leu Thr
65                  70                  75                  80

Pro Gln Ala Tyr Ala Val Ile Ser Gly Ala Pro Ala Ala Ile Ala Gly
                85                  90                  95

Phe Ala Ala Leu Leu Gln Thr Val Thr Gly Val Ser Ala Val Ala Gln
            100                 105                 110

Val Gly Tyr Arg Phe Phe Ser Asp Trp Asp His Lys Val Ser Thr Val
        115                 120                 125

Gly Leu Tyr Gln Gln Pro Gly Met Ala Val Asp Leu Tyr Arg Pro Asp
    130                 135                 140

Asp Tyr Tyr Asp Ile Leu Phe Pro Gly Val Gln Thr Phe Val His Ser
145                 150                 155                 160
```

-continued

```
Val Gln Tyr Leu Asp Pro Arg His Trp Gly Pro Thr Leu Phe Asn Ala
            165                 170                 175

Ile Ser Gln Ala Phe Trp Arg Val Ile Gln Asn Asp Ile Pro Arg Leu
        180                 185                 190

Thr Ser Gln Glu Leu Glu Arg Arg Thr Gln Arg Tyr Leu Arg Asp Ser
    195                 200                 205

Leu Ala Arg Phe Leu Glu Glu Thr Thr Trp Thr Val Ile Asn Ala Pro
210                 215                 220

Val Asn Trp Tyr Asn Ser Leu Gln Asp Tyr Tyr Ser Thr Leu Ser Pro
225                 230                 235                 240

Ile Arg Pro Thr Met Val Arg Gln Val Ala Asn Arg Glu Gly Leu Gln
                245                 250                 255

Ile Ser Phe Gly His Thr Tyr Asp Asn Ile Asp Glu Ala Asp Ser Ile
            260                 265                 270

Gln Gln Val Thr Glu Arg Trp Glu Ala Gln Ser Gln Ser Pro Asn Val
        275                 280                 285

Gln Ser Gly Glu Phe Ile Glu Lys Phe Glu Ala Pro Gly Gly Ala Asn
    290                 295                 300

Gln Arg Thr Ala Pro Gln Trp Met Leu Pro Leu Leu Leu Gly Leu Tyr
305                 310                 315                 320

Gly Ser Val Thr Ser Ala Leu Lys Ala Tyr Glu Asp Gly Pro Asn Lys
                325                 330                 335

Lys Lys Arg Lys Leu Ser Arg Gly Ser Ser Gln Lys Thr Lys Gly Thr
            340                 345                 350

Ser Ala Ser Ala Lys Ala Arg His Lys Arg Arg Asn Arg Ser Ser Arg
        355                 360                 365

Ser Glu Phe Gly Gly Gly Ser Gly Gly Gly Ser Gly Gly Gly
    370                 375                 380

Gly Ser Met Gly Ser Ile Gly Ala Ala Ser Met Glu Phe Cys Phe Asp
385                 390                 395                 400

Val Phe Lys Glu Leu Lys Val His His Ala Asn Glu Asn Ile Phe Tyr
                405                 410                 415

Cys Pro Ile Ala Ile Met Ser Ala Leu Ala Met Val Tyr Leu Gly Ala
            420                 425                 430

Lys Asp Ser Thr Arg Thr Gln Ile Asn Lys Val Val Arg Phe Asp Lys
        435                 440                 445

Leu Pro Gly Phe Gly Asp Ser Ile Glu Ala Gln Cys Gly Thr Ser Val
    450                 455                 460

Asn Val His Ser Ser Leu Arg Asp Ile Leu Asn Gln Ile Thr Lys Pro
465                 470                 475                 480

Asn Asp Val Tyr Ser Phe Ser Leu Ala Ser Arg Leu Tyr Ala Glu Glu
                485                 490                 495

Arg Tyr Pro Ile Leu Pro Glu Tyr Leu Gln Cys Val Lys Glu Leu Tyr
            500                 505                 510

Arg Gly Gly Leu Glu Pro Ile Asn Phe Gln Thr Ala Ala Asp Gln Ala
        515                 520                 525

Arg Glu Leu Ile Asn Ser Trp Val Glu Ser Gln Thr Asn Gly Ile Ile
    530                 535                 540

Arg Asn Val Leu Gln Pro Ser Ser Val Asp Ser Gln Thr Ala Met Val
545                 550                 555                 560

Leu Val Asn Ala Ile Val Phe Lys Gly Leu Trp Glu Lys Ala Phe Lys
                565                 570                 575
```

Asp Glu Asp Thr Gln Ala Met Pro Phe Arg Val Thr Glu Gln Ser
              580                 585                 590
Lys Pro Val Gln Met Met Tyr Gln Ile Gly Leu Phe Arg Val Ala Ser
        595                 600                 605
Met Ala Ser Glu Lys Met Lys Ile Leu Glu Leu Pro Phe Ala Ser Gly
        610                 615                 620
Thr Met Ser Met Leu Val Leu Leu Pro Asp Glu Val Ser Gly Leu Glu
625                 630                 635                 640
Gln Leu Glu Ser Ile Ile Asn Phe Glu Lys Leu Thr Glu Trp Thr Ser
                645                 650                 655
Ser Asn Val Met Glu Glu Arg Lys Ile Lys Val Tyr Leu Pro Arg Met
            660                 665                 670
Lys Met Glu Glu Lys Tyr Asn Leu Thr Ser Val Leu Met Ala Met Gly
        675                 680                 685
Ile Thr Asp Val Phe Ser Ser Ser Ala Asn Leu Ser Gly Ile Ser Ser
    690                 695                 700
Ala Glu Ser Leu Lys Ile Ser Gln Ala Val His Ala Ala His Ala Glu
705                 710                 715                 720
Ile Asn Glu Ala Gly Arg Glu Val Val Gly Ser Ala Glu Ala Gly Val
                725                 730                 735
Asp Ala Ala Ser Val Ser Glu Glu Phe Arg Ala Asp His Pro Phe Leu
            740                 745                 750
Phe Cys Ile Lys His Ile Ala Thr Asn Ala Val Leu Phe Phe Gly Arg
        755                 760                 765
Cys Val Ser Pro
        770

<210> SEQ ID NO 7
<211> LENGTH: 2319
<212> TYPE: DNA
<213> ORGANISM: Artificial Sequence
<220> FEATURE:
<223> OTHER INFORMATION: Synthetic polynucleotide - gene encoding VP2
      fused with OVA via a GS linker

<400> SEQUENCE: 7

| | | | | | |
|---|---|---|---|---|---|
| atgggcagca | gcgactacaa | ggacgacgat | gacaagagca | gcggcacgcg | tatgggtgct | 60 |
| gctttaacac | tgttggggga | cctaattgct | actgtgtctg | aagctgctgc | tgctactgga | 120 |
| ttttcagtag | ctgaaattgc | tgctggagag | ccgctgctg | caattgaagt | gcaacttgca | 180 |
| tctgttgcta | ctgttgaagg | cctaacaacc | tctgaggcaa | ttgctgctat | aggcctcact | 240 |
| ccacaggcct | atgctgtgat | atctggggct | cctgctgcta | tagctggatt | tgcagcttta | 300 |
| ctgcaaactg | tgactggtgt | gagcgctgtt | gctcaagtgg | ggtatagatt | ttttagtgac | 360 |
| tgggatcaca | aagtttctac | tgttggttta | atcaacaac | caggaatggc | tgtagatttg | 420 |
| tataggccag | atgattacta | tgatattttta | tttcctggag | tacaaacctt | tgttcacagt | 480 |
| gttcagtatc | ttgaccccag | acattggggt | ccaacacttt | taatgccat | ttctcaagct | 540 |
| ttttggcgtg | taatacaaaa | tgacattcct | aggctcacct | cacaggagct | gaaagaaga | 600 |
| acccaaagat | atttaaggga | cagtttggca | aggttttttag | aggaaactac | ttggacagta | 660 |
| attaatgctc | ctgttaattg | gtataactct | ttacaagatt | actactctac | tttgtctccc | 720 |
| attaggccta | caatggtgag | acaagtagcc | aacagggaag | ggttgcaaat | atcatttggg | 780 |
| cacacctatg | ataatattga | tgaagcagac | agtattcagc | aagtaactga | gaggtgggaa | 840 |
| gctcaaagcc | aaagtcctaa | tgtgcagtca | ggtgaattta | ttgaaaaatt | tgaggctcct | 900 |

| | |
|---|---|
| ggtggtgcaa atcaaagaac tgctcctcag tggatgttgc ctttacttct aggcctgtac | 960 |
| ggaagtgtta cttctgctct aaaagcttat gaagatggcc ccaacaaaaa gaaaaggaag | 1020 |
| ttgtccaggg gcagctccca aaaaaccaaa ggaaccagtg caagtgccaa agctcgtcat | 1080 |
| aaaaggagga atagaagttc taggagtgaa ttcggtggtg gtggaagtgg tggtggtgga | 1140 |
| agtggtggtg gtggaagtat gggcagcatc ggcgccgcca gcatggagtt ctgcttcgac | 1200 |
| gtgttcaagg agctgaaggt gcaccacgcc aacgagaaca tcttctactg ccccatcgcc | 1260 |
| atcatgagcg ccctggccat ggtgtacctg ggcgccaagg acagcaccag gacccagatc | 1320 |
| aacaaggtgg tgaggttcga caagctgccc ggcttcggcg acagcatcga ggcccagtgc | 1380 |
| ggcaccagcg tgaacgtgca cagcagcctg agggacatcc tgaaccagat caccaagccc | 1440 |
| aacgacgtgt acagcttcag cctggccagc aggctgtacg ccgaggagag gtaccccatc | 1500 |
| ctgcccgagt acctgcagtg cgtgaaggag ctgtacaggg gcggcctgga gcccatcaac | 1560 |
| ttccagaccg ccgccgacca ggccagggag ctgatcaaca gctgggtgga gagccagacc | 1620 |
| aacggcatca tcaggaacgt gctgcagccc agcagcgtgg acagcagac cgccatggtg | 1680 |
| ctggtgaacg ccatcgtgtt caagggcctg tgggagaagg ccttcaagga cgaggacacc | 1740 |
| caggccatgc ccttcagggt gaccgagcag gagagcaagc ccgtgcagat gatgtaccag | 1800 |
| atcggcctgt tcagggtggc cagcatggcc agcgagaaga tgaagatcct ggagctgccc | 1860 |
| ttcgccagcg gcaccatgag catgctggtg ctgctgcccg acgaggtgag cggcctggag | 1920 |
| cagctggaga gcatcatcaa cttcgagaag ctgaccgagt ggaccagcag caacgtgatg | 1980 |
| gaggagagga agatcaaggt gtacctgccc aggatgaaga tggaggagaa gtacaacctg | 2040 |
| accagcgtgc tgatggccat gggcatcacc gacgtgttca gcagcagcgc caacctgagc | 2100 |
| ggaatcagca gcgccgagag cctgaagatc agccaggctg tgcacgctgc tcacgctgag | 2160 |
| atcaacgagg ctggaaggga ggtggtggga agcgccgagg ctggagtgga cgctgccagc | 2220 |
| gtgagcgagg agttcagggc cgaccacccc ttcctgttct gcatcaagca catcgccacc | 2280 |
| aacgccgtgc tgttcttcgg caggtgcgtg agcccctga | 2319 |

<210> SEQ ID NO 8
<211> LENGTH: 36
<212> TYPE: PRT
<213> ORGANISM: Polyomavirus SV40

<400> SEQUENCE: 8

```
Ser Gly Glu Phe Ile Glu Lys Phe Glu Ala Pro Gly Gly Ala Asn Gln
1               5                   10                  15
Arg Thr Ala Pro Gln Trp Met Leu Pro Leu Leu Leu Gly Leu Tyr Gly
            20                  25                  30
Ser Val Thr Ser
        35
```

<210> SEQ ID NO 9
<211> LENGTH: 234
<212> TYPE: PRT
<213> ORGANISM: Polyomavirus SV40

<400> SEQUENCE: 9

```
Met Ala Val Asp Leu Tyr Arg Pro Asp Asp Tyr Tyr Asp Ile Leu Phe
1               5                   10                  15
Pro Gly Val Gln Thr Phe Val His Ser Val Gln Tyr Leu Asp Pro Arg
            20                  25                  30
```

His Trp Gly Pro Thr Leu Phe Asn Ala Ile Ser Gln Ala Phe Trp Arg
         35                  40                  45

Val Ile Gln Asn Asp Ile Pro Arg Leu Thr Ser Gln Glu Leu Glu Arg
 50                  55                  60

Arg Thr Gln Arg Tyr Leu Arg Asp Ser Leu Ala Arg Phe Leu Glu Glu
 65                  70                  75                  80

Thr Thr Trp Thr Val Ile Asn Ala Pro Val Asn Trp Tyr Asn Ser Leu
                 85                  90                  95

Gln Asp Tyr Tyr Ser Thr Leu Ser Pro Ile Arg Pro Thr Met Val Arg
             100                 105                 110

Gln Val Ala Asn Arg Glu Gly Leu Gln Ile Ser Phe Gly His Thr Tyr
             115                 120                 125

Asp Asn Ile Asp Glu Ala Asp Ser Ile Gln Gln Val Thr Glu Arg Trp
         130                 135                 140

Glu Ala Gln Ser Gln Ser Pro Asn Val Gln Ser Gly Glu Phe Ile Glu
145                 150                 155                 160

Lys Phe Glu Ala Pro Gly Gly Ala Asn Gln Arg Thr Ala Pro Gln Trp
                 165                 170                 175

Met Leu Pro Leu Leu Leu Gly Leu Tyr Gly Ser Val Thr Ser Ala Leu
             180                 185                 190

Lys Ala Tyr Glu Asp Gly Pro Asn Lys Lys Arg Lys Leu Ser Arg
             195                 200                 205

Gly Ser Ser Gln Lys Thr Lys Gly Thr Ser Ala Ser Ala Lys Ala Arg
             210                 215                 220

His Lys Arg Arg Asn Arg Ser Ser Arg Ser
225                 230

<210> SEQ ID NO 10
<211> LENGTH: 705
<212> TYPE: DNA
<213> ORGANISM: Polyomavirus SV40

<400> SEQUENCE: 10
atggctgtag atttgtatag gccagatgat tactatgata ttttatttcc tggagtacaa      60
acctttgttc acagtgttca gtatcttgac cccagacatt ggggtccaac acttttttaat    120 gccatttctc aagcttttttg gcgtgtaata caaaatgaca ttcctaggct cacctcacag    180
gagcttgaaa aagaacccca aagatattta agggacagtt tggcaaggtt tttagaggaa    240
actacttgga cagtaattaa tgctcctgtt aattggtata ctctttttaca agattactac    300 tctacttttgt ctcccattag gcctacaatg gtgagacaag tagccaacag gaagggttg      360 caaatatcat ttgggcacac ctatgataat attgatgaag cagacagtat tcagcaagta    420
actgagaggt gggaagctca aagccaaagt cctaatgtgc agtcaggtga atttattgaa    480
aaatttgagg ctcctggtgg tgcaaatcaa agaactgctc ctcagtggat gttgccttta    540
cttctaggcc tgtacggaag tgttacttct gctctaaaag cttatgaaga tggccccaac    600
aaaaagaaaa ggaagttgtc cagggggcagc tcccaaaaaa ccaaaggaac cagtgcaagt    660
gccaaagctc gtcataaaag gaggaataga agttctagga gttaa                   705

<210> SEQ ID NO 11
<211> LENGTH: 352
<212> TYPE: PRT
<213> ORGANISM: Polyomavirus SV40

<400> SEQUENCE: 11

| | | | | | | | | | | | | | | |
|---|---|---|---|---|---|---|---|---|---|---|---|---|---|---|
| Met | Gly | Ala | Ala | Leu | Thr | Leu | Leu | Gly | Asp | Leu | Ile | Ala | Thr | Val | Ser |
| 1 | | | | 5 | | | | | 10 | | | | | 15 | |
| Glu | Ala | Ala | Ala | Ala | Thr | Gly | Phe | Ser | Val | Ala | Glu | Ile | Ala | Ala | Gly |
| | | 20 | | | | | 25 | | | | | 30 | | | |
| Glu | Ala | Ala | Ala | Ala | Ile | Glu | Val | Gln | Leu | Ala | Ser | Val | Ala | Thr | Val |
| | | | 35 | | | | | 40 | | | | | 45 | | |
| Glu | Gly | Leu | Thr | Thr | Ser | Glu | Ala | Ile | Ala | Ala | Ile | Gly | Leu | Thr | Pro |
| | 50 | | | | | 55 | | | | | 60 | | | | |
| Gln | Ala | Tyr | Ala | Val | Ile | Ser | Gly | Ala | Pro | Ala | Ala | Ile | Ala | Gly | Phe |
| 65 | | | | | 70 | | | | | 75 | | | | | 80 |
| Ala | Ala | Leu | Leu | Gln | Thr | Val | Thr | Gly | Val | Ser | Ala | Val | Ala | Gln | Val |
| | | | | 85 | | | | | 90 | | | | | 95 | |
| Gly | Tyr | Arg | Phe | Phe | Ser | Asp | Trp | Asp | His | Lys | Val | Ser | Thr | Val | Gly |
| | | | 100 | | | | | 105 | | | | | 110 | | |
| Leu | Tyr | Gln | Gln | Pro | Gly | Met | Ala | Val | Asp | Leu | Tyr | Arg | Pro | Asp | Asp |
| | | | 115 | | | | | 120 | | | | | 125 | | |
| Tyr | Tyr | Asp | Ile | Leu | Phe | Pro | Gly | Val | Gln | Thr | Phe | Val | His | Ser | Val |
| | 130 | | | | | 135 | | | | | 140 | | | | |
| Gln | Tyr | Leu | Asp | Pro | Arg | His | Trp | Gly | Pro | Thr | Leu | Phe | Asn | Ala | Ile |
| 145 | | | | | 150 | | | | | 155 | | | | | 160 |
| Ser | Gln | Ala | Phe | Trp | Arg | Val | Ile | Gln | Asn | Asp | Ile | Pro | Arg | Leu | Thr |
| | | | | 165 | | | | | 170 | | | | | 175 | |
| Ser | Gln | Glu | Leu | Glu | Arg | Arg | Thr | Gln | Arg | Tyr | Leu | Arg | Asp | Ser | Leu |
| | | | 180 | | | | | 185 | | | | | 190 | | |
| Ala | Arg | Phe | Leu | Glu | Glu | Thr | Thr | Trp | Thr | Val | Ile | Asn | Ala | Pro | Val |
| | | 195 | | | | | 200 | | | | | 205 | | | |
| Asn | Trp | Tyr | Asn | Ser | Leu | Gln | Asp | Tyr | Tyr | Ser | Thr | Leu | Ser | Pro | Ile |
| | 210 | | | | | 215 | | | | | 220 | | | | |
| Arg | Pro | Thr | Met | Val | Arg | Gln | Val | Ala | Asn | Arg | Glu | Gly | Leu | Gln | Ile |
| 225 | | | | | 230 | | | | | 235 | | | | | 240 |
| Ser | Phe | Gly | His | Thr | Tyr | Asp | Asn | Ile | Asp | Glu | Ala | Asp | Ser | Ile | Gln |
| | | | | 245 | | | | | 250 | | | | | 255 | |
| Gln | Val | Thr | Glu | Arg | Trp | Glu | Ala | Gln | Ser | Gln | Ser | Pro | Asn | Val | Gln |
| | | | 260 | | | | | 265 | | | | | 270 | | |
| Ser | Gly | Glu | Phe | Ile | Glu | Lys | Phe | Glu | Ala | Pro | Gly | Gly | Ala | Asn | Gln |
| | | 275 | | | | | 280 | | | | | 285 | | | |
| Arg | Thr | Ala | Pro | Gln | Trp | Met | Leu | Pro | Leu | Leu | Leu | Gly | Leu | Tyr | Gly |
| | 290 | | | | | 295 | | | | | 300 | | | | |
| Ser | Val | Thr | Ser | Ala | Leu | Lys | Ala | Tyr | Glu | Asp | Gly | Pro | Asn | Lys | Lys |
| 305 | | | | | 310 | | | | | 315 | | | | | 320 |
| Lys | Arg | Lys | Leu | Ser | Arg | Gly | Ser | Ser | Gln | Lys | Thr | Lys | Gly | Thr | Ser |
| | | | | 325 | | | | | 330 | | | | | 335 | |
| Ala | Ser | Ala | Lys | Ala | Arg | His | Lys | Arg | Arg | Asn | Arg | Ser | Ser | Arg | Ser |
| | | | 340 | | | | | 345 | | | | | 350 | | |

<210> SEQ ID NO 12
<211> LENGTH: 1059
<212> TYPE: DNA
<213> ORGANISM: Polyomavirus SV40

<400> SEQUENCE: 12
atgggtgctg ctttaacact gttgggggac ctaattgcta ctgtgtctga agctgctgct    60
gctactggat tttcagtagc tgaaattgct gctggagagg ccgctgctgc aattgaagtg   120

```
caacttgcat ctgttgctac tgttgaaggc ctaacaacct ctgaggcaat tgctgctata      180
ggcctcactc cacaggccta tgctgtgata tctggggctc ctgctgctat agctggattt      240
gcagctttac tgcaaactgt gactggtgtg agcgctgttg ctcaagtggg gtatagattt      300
tttagtgact gggatcacaa agtttctact gttggtttat atcaacaacc aggaatggct      360
gtagatttgt ataggccaga tgattactat gatatttat ttcctggagt acaaaccttt       420
gttcacagtg ttcagtatct tgaccccaga cattggggtc aaacacttttt taatgccatt     480 tctcaagctt tttggcgtgt aatacaaaat gacattccta ggctcacctc acaggagctt      540
gaaagaagaa cccaaagata tttaagggac agtttggcaa ggttttttaga ggaaactact    600 tggacagtaa ttaatgctcc tgttaattgg tataactctt tacaagatta ctactctact      660
ttgtctccca ttaggcctac aatggtgaga caagtagcca acaggaaggg gttgcaaata     720
tcatttgggc acacctatga taatattgat gaagcagaca gtattcagca agtaactgag      780
aggtgggaag ctcaaagcca aagtcctaat gtgcagtcag gtgaatttat tgaaaaattt      840
gaggctcctg gtggtgcaaa tcaaagaact gctcctcagt ggatgttgcc tttacttcta      900
ggcctgtacg gaagtgttac ttctgctcta aaagcttatg aagatggccc caacaaaaag      960
aaaaggaagt tgtccagggg cagctcccaa aaaccaaag gaaccagtgc aagtgccaaa     1020
gctcgtcata aaggaggaa tagaagttct aggagttaa                             1059

<210> SEQ ID NO 13
<211> LENGTH: 24
<212> TYPE: DNA
<213> ORGANISM: Artificial Sequence
<220> FEATURE:
<223> OTHER INFORMATION: Synthetic polynucleotide sequence encoding FLAG
      tag

<400> SEQUENCE: 13
gactacaagg acgacgatga caag                                            24

<210> SEQ ID NO 14
<211> LENGTH: 45
<212> TYPE: DNA
<213> ORGANISM: Artificial Sequence
<220> FEATURE:
<223> OTHER INFORMATION: Synthetic polynucleotide sequence encoding GS
      linker

<400> SEQUENCE: 14
ggtggtggtg gaagtggtgg tggtggaagt ggtggtggtg gaagt                     45

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Gly Ile Leu Gly Phe Val Phe Thr Leu
1               5

<210> SEQ ID NO 16
<211> LENGTH: 71
<212> TYPE: DNA
<213> ORGANISM: Artificial Sequence
<220> FEATURE:
<223> OTHER INFORMATION: Synthetic nucleotide sequence
```

-continued

```
<400> SEQUENCE: 16
tataaataga tcttggtacc cgggaattcg agctcctcga ggcggccgcc ctgcaggata    60
tctctagata c                                                         71
```